US007811286B2

(12) United States Patent
Medoff

(10) Patent No.: US 7,811,286 B2
(45) Date of Patent: Oct. 12, 2010

(54) IMPLANT DEVICE FOR APPLYING COMPRESSION ACROSS A FRACTURE SITE

(75) Inventor: Robert J. Medoff, 159 Kuukama St., Kailua, HI (US) 96734

(73) Assignees: Robert J. Medoff, Kailua, HI (US); Lars G. Tellman, Falsterbo (SE); David Medoff, Valencia, CA (US)

( * ) Notice: Subject to any disclaimer, the term of this patent is extended or adjusted under 35 U.S.C. 154(b) by 1159 days.

(21) Appl. No.: 11/377,605

(22) Filed: Mar. 16, 2006

(65) Prior Publication Data
US 2006/0189992 A1 Aug. 24, 2006

Related U.S. Application Data

(63) Continuation-in-part of application No. 10/073,826, filed on Feb. 11, 2002, now Pat. No. 7,037,308.

(60) Provisional application No. 60/268,099, filed on Feb. 12, 2001.

(51) Int. Cl.
*A61B 17/58* (2006.01)
(52) U.S. Cl. .................. 606/75; 606/64; 606/151
(58) Field of Classification Search .......... 606/75, 606/158, 157, 151, 143, 324, 64; 24/115 A, 24/703.1, 326
See application file for complete search history.

(56) References Cited

U.S. PATENT DOCUMENTS

| 565,255 | A | 8/1896 | Belden |
| 583,455 | A | 6/1897 | Bush |
| 1,608,790 | A | 11/1926 | Geoffrey |
| 2,031,483 | A | 2/1936 | Interrante |
| 2,031,484 | A | 2/1936 | Interrante |
| 3,939,828 | A | 2/1976 | Mohr et al. |
| 4,409,970 | A | 10/1983 | Carrel |
| 4,658,822 | A | 4/1987 | Kees |
| 4,838,254 | A | 6/1989 | Gauthier |
| 4,852,559 | A | 8/1989 | Chernoff |

(Continued)

FOREIGN PATENT DOCUMENTS

EP 0 693 272 A 1/1996

(Continued)

OTHER PUBLICATIONS

Translation of Pertinent Part of 0 693 272 A Jan. 24, 1996.

*Primary Examiner*—Pedro Philogene
(74) *Attorney, Agent, or Firm*—Ladas & Parry LLP

(57) ABSTRACT

A fracture fixation implant formed from a single piece of material bent in loop form to provide juxtaposed first and second legs joined by a bend. The first leg is dimensional and configured to be implanted within a bone to extend across a fracture in the bone, the second leg extending backwardly from the bend and having a length to extend on an outer surface of the bone across the fracture. The implant exits from the bone at the bend, such that application of a pulling force on the second leg produces compression across the fracture. The second leg is flat and is provided with a plurality of holes in which bone screws can be installed to secure the second leg directly to the bone and maintain the compression across the fracture. The implant avoids the use of washers.

32 Claims, 21 Drawing Sheets

U.S. PATENT DOCUMENTS

| | | | |
|---|---|---|---|
| 5,013,314 A | 5/1991 | Firica et al. | |
| 5,092,889 A | 3/1992 | Campbell | |
| 5,312,426 A | 5/1994 | Segawa et al. | |
| 5,372,604 A | 12/1994 | Trott | |
| 5,374,268 A | 12/1994 | Sander | |
| 5,441,509 A | 8/1995 | Vidal et al. | |
| 5,487,746 A | 1/1996 | Yu et al. | |
| 5,507,747 A | 4/1996 | Yuan et al. | |
| 5,620,452 A * | 4/1997 | Yoon | 606/151 |
| 5,709,682 A | 1/1998 | Medoff | |
| 5,976,134 A * | 11/1999 | Huebner | 606/59 |
| 6,066,141 A | 5/2000 | Dall et al. | |
| 6,248,109 B1 | 6/2001 | Stoffella | |
| 6,302,884 B1 | 10/2001 | Wellisz et al. | |
| 6,464,710 B1 | 10/2002 | Foster | |
| 6,554,835 B1 | 4/2003 | Lee | |
| 6,716,226 B2 * | 4/2004 | Sixto et al. | 606/157 |
| 2002/0095157 A1 | 7/2002 | Bowman | |

FOREIGN PATENT DOCUMENTS

| | | | |
|---|---|---|---|
| EP | 0693272 | * | 1/1996 |

* cited by examiner

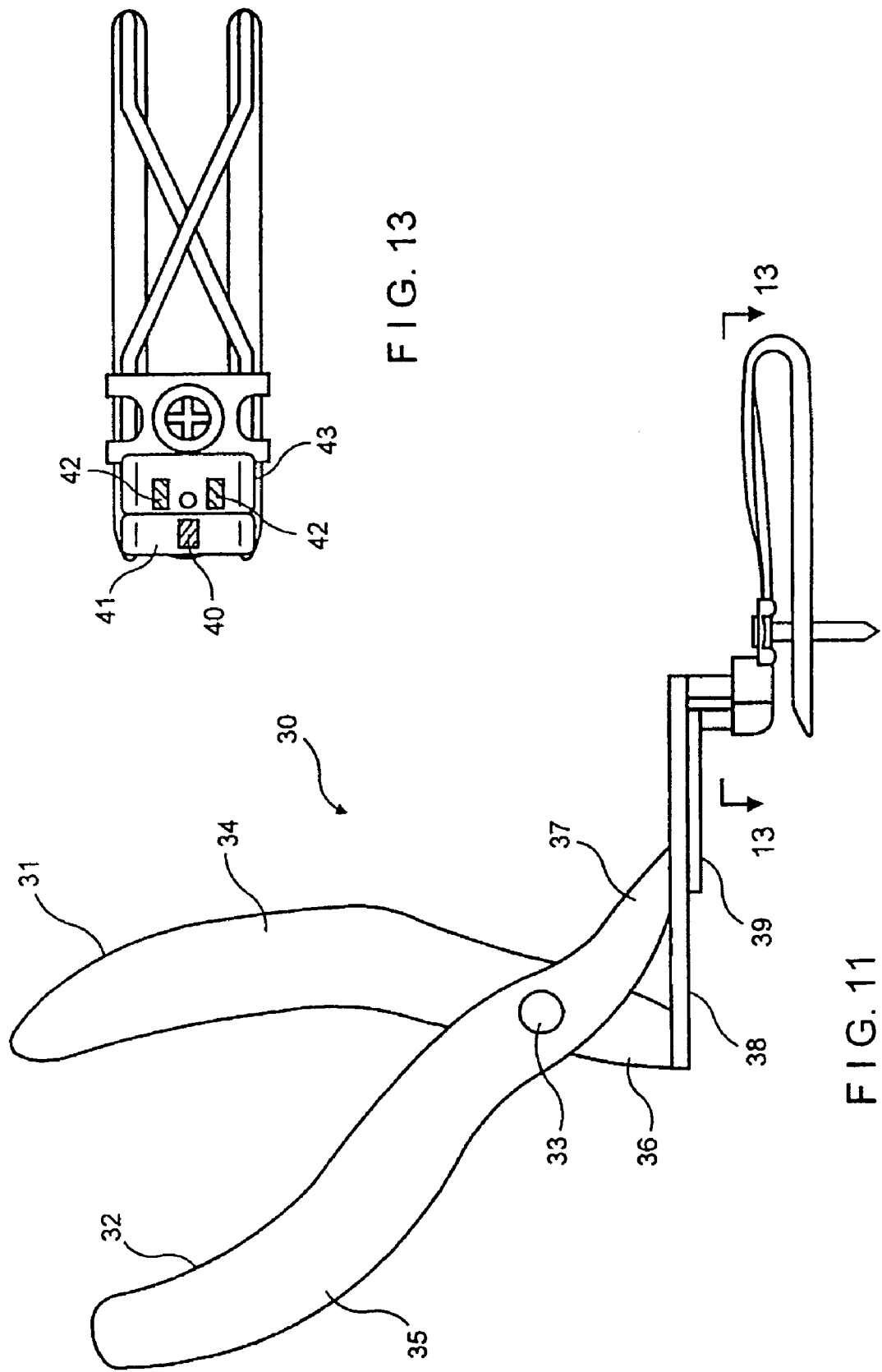

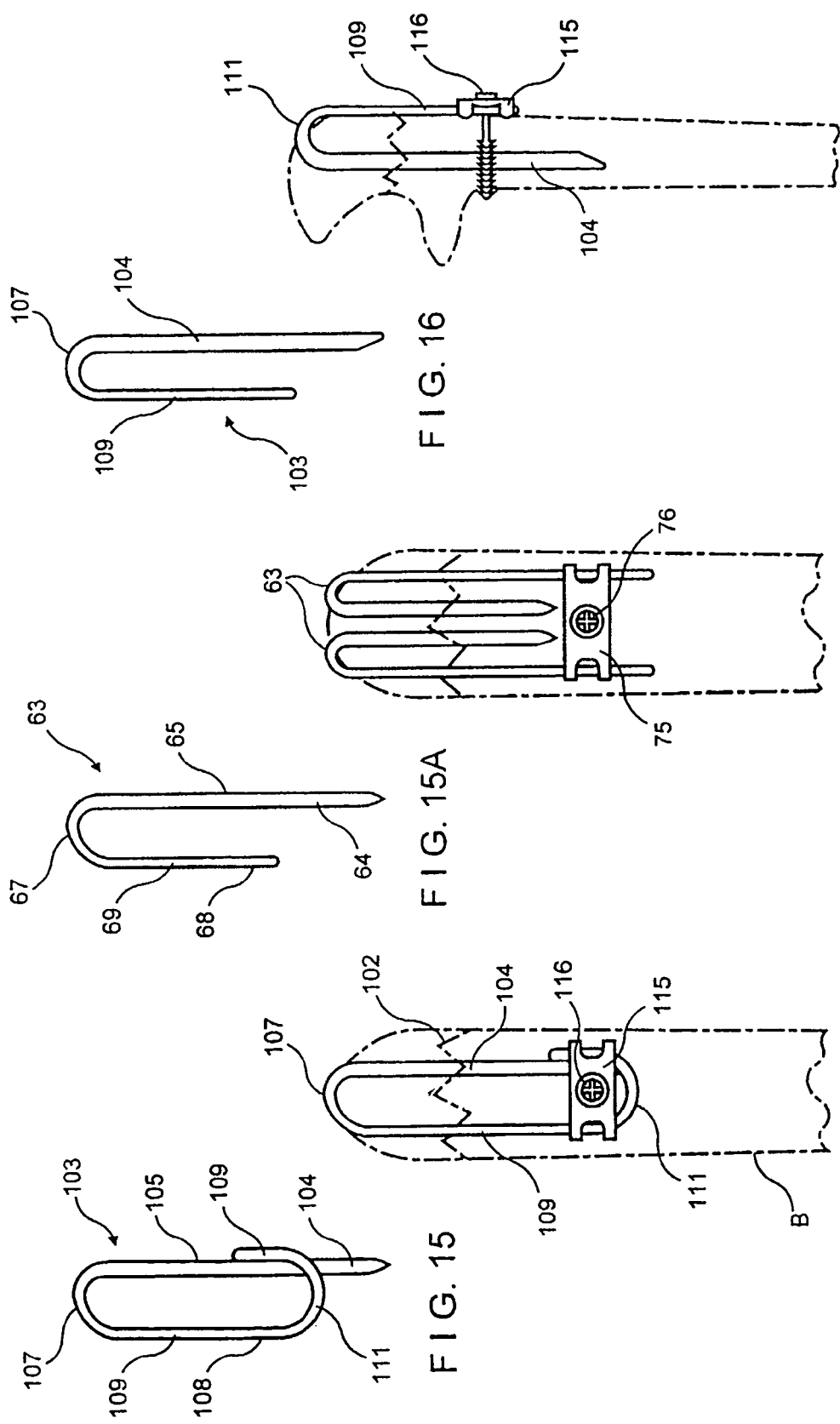

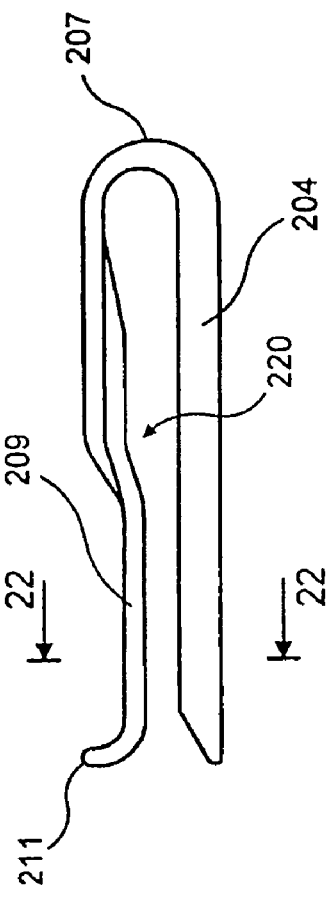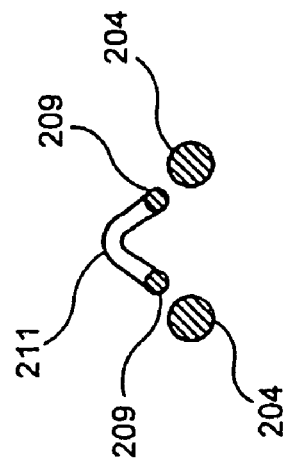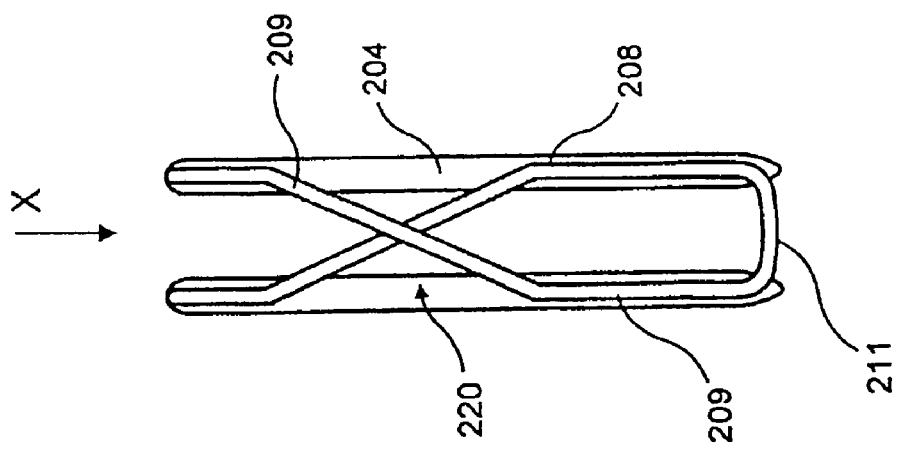

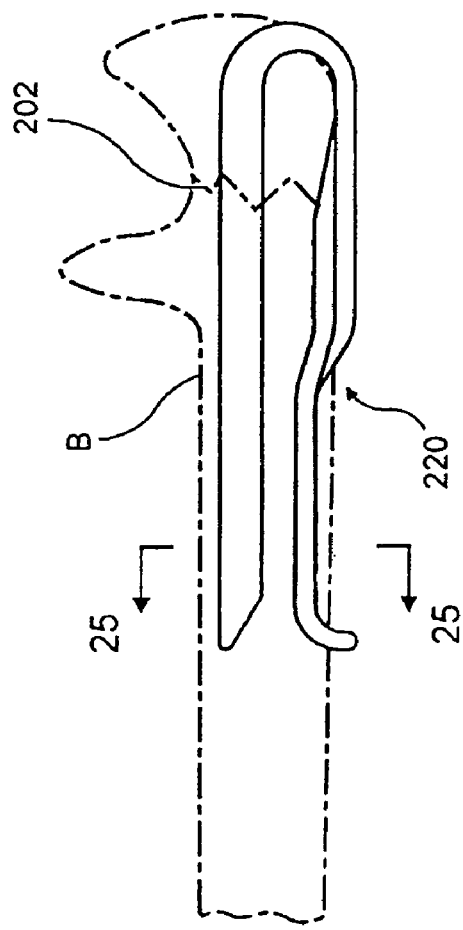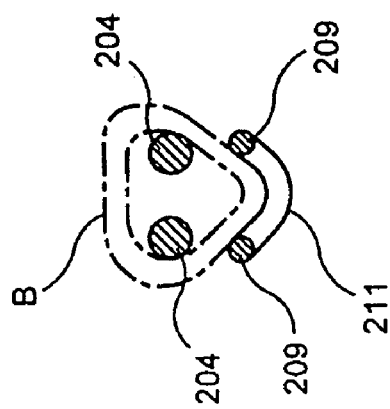

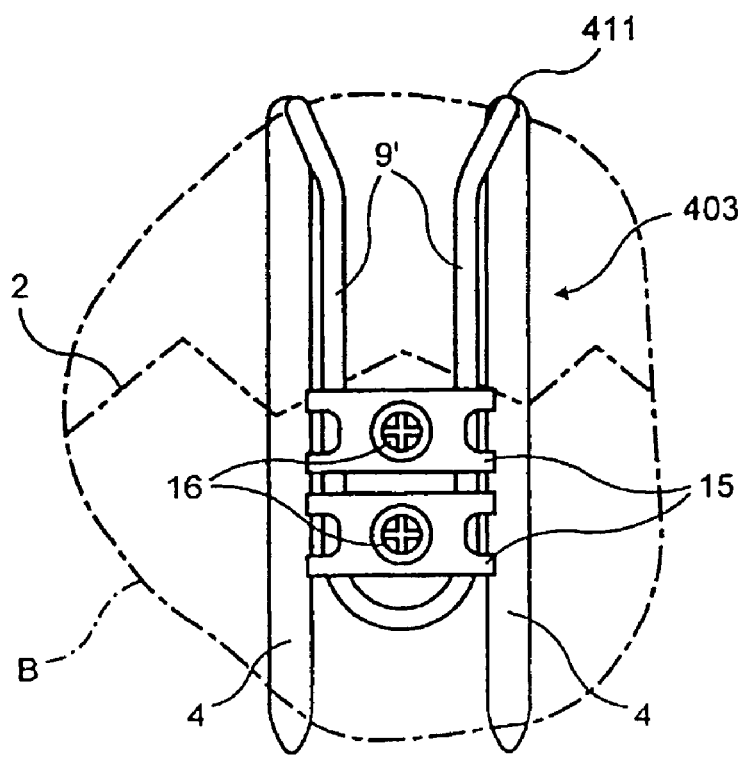
F I G. 30
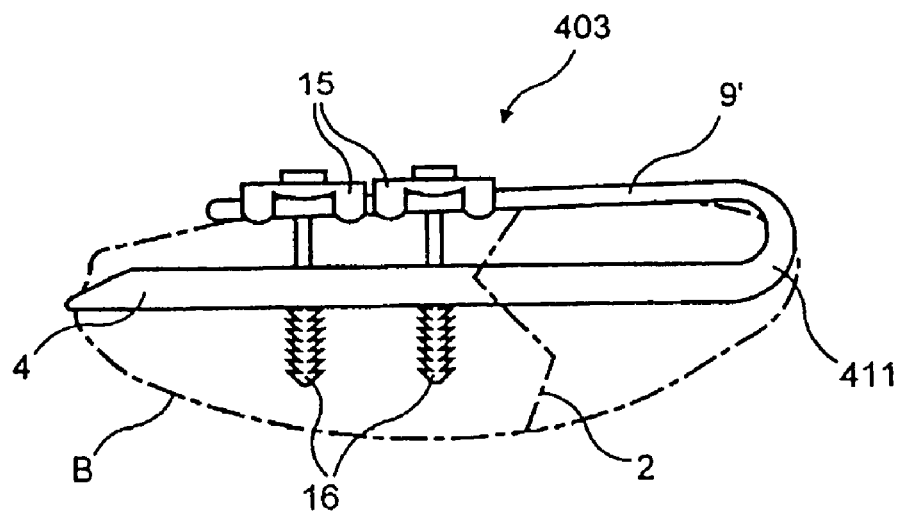
F I G. 31

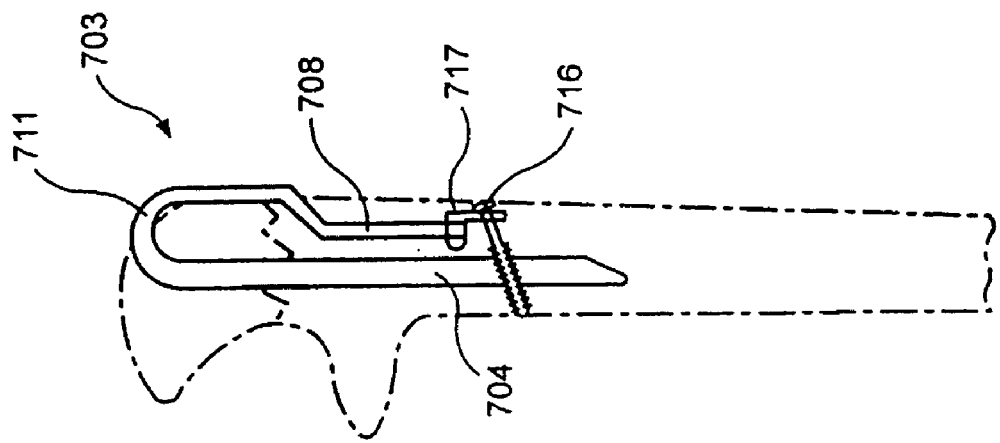
FIG. 41
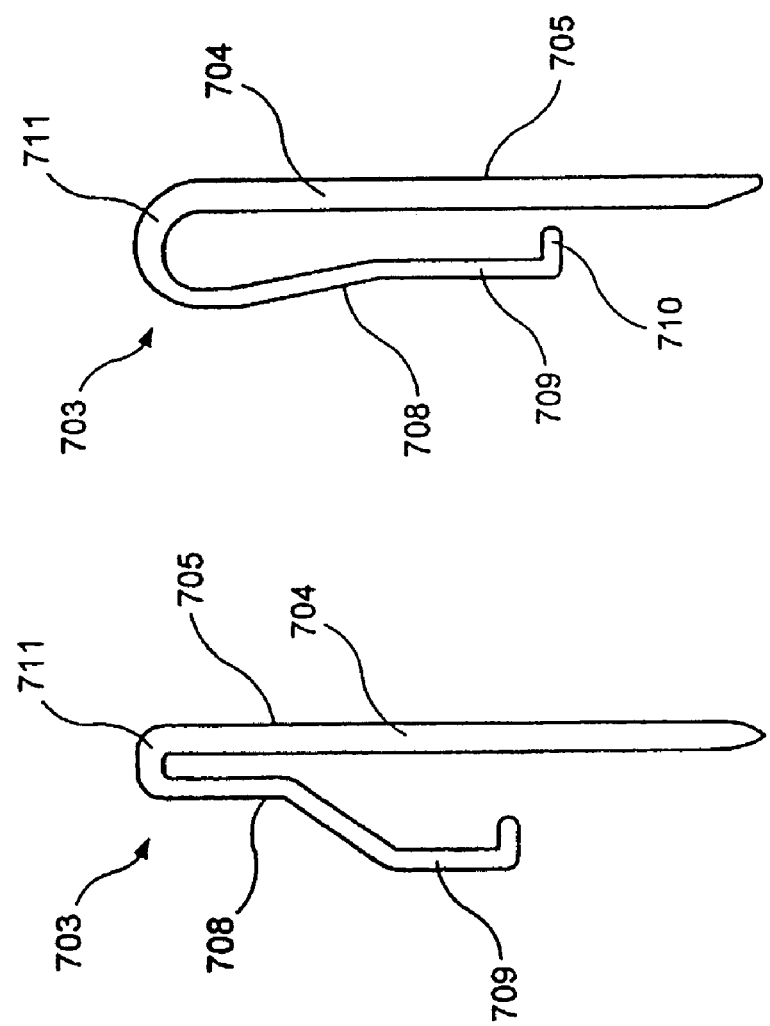
FIG. 37
FIG. 36

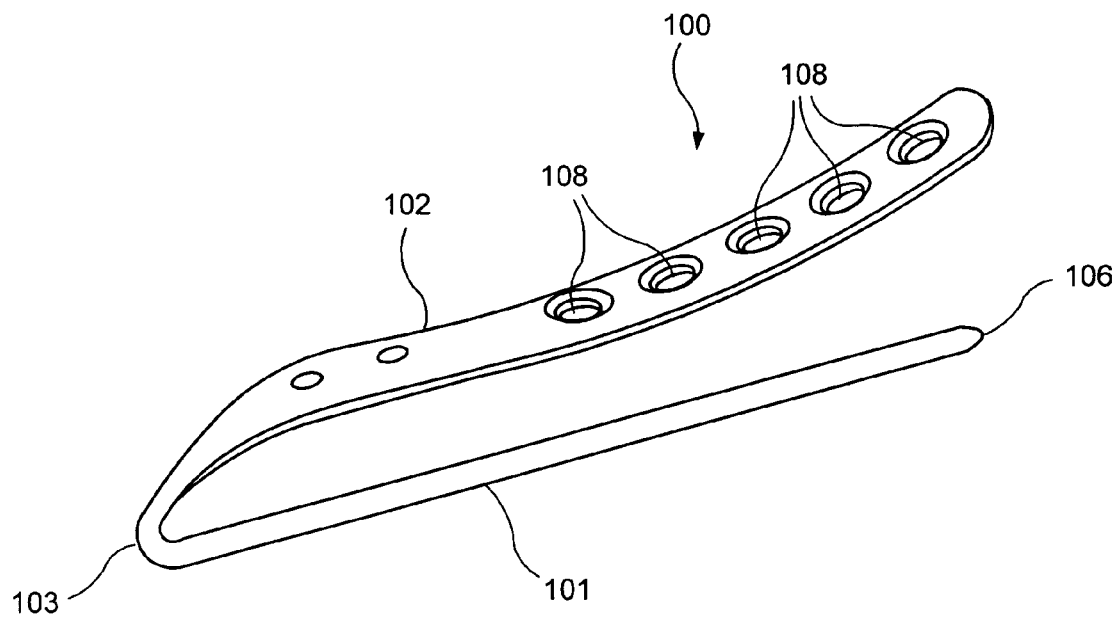
F I G. 42
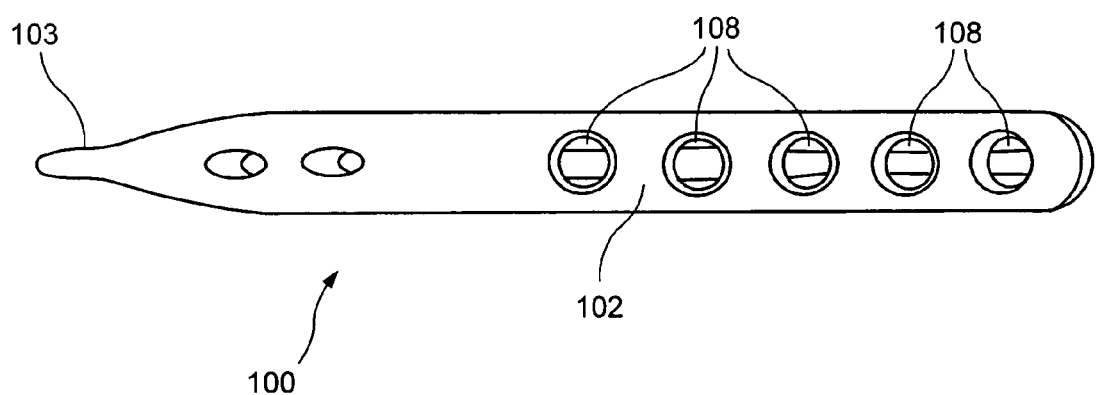
F I G. 43

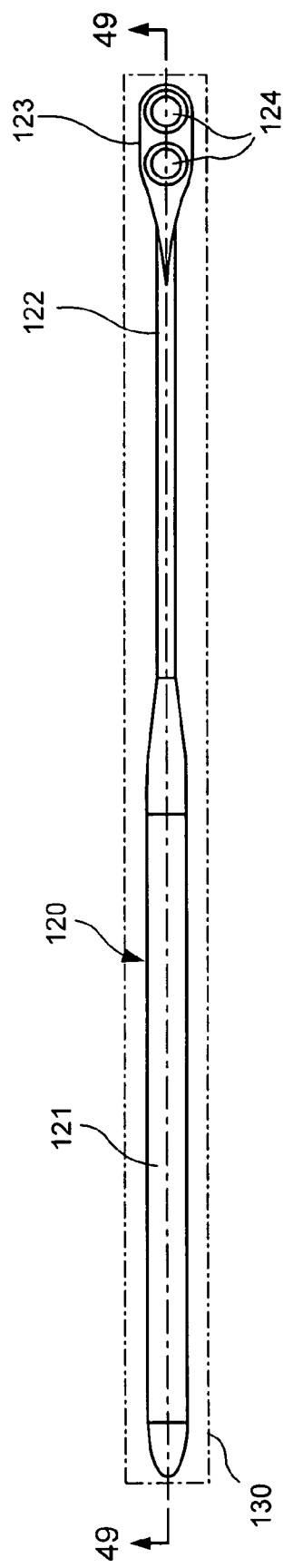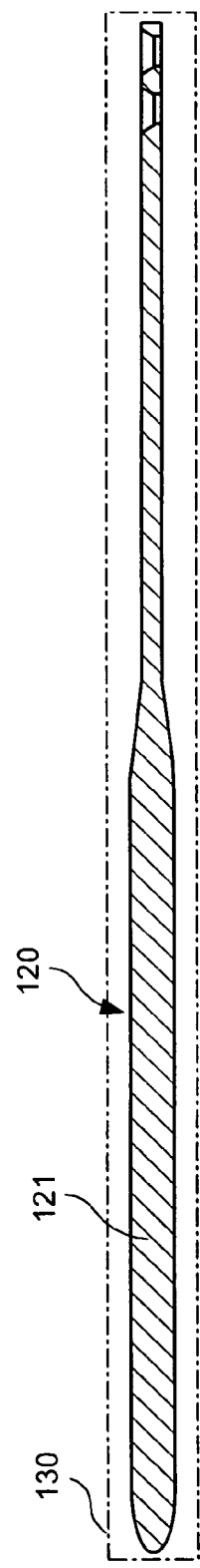
FIG. 48
FIG. 49

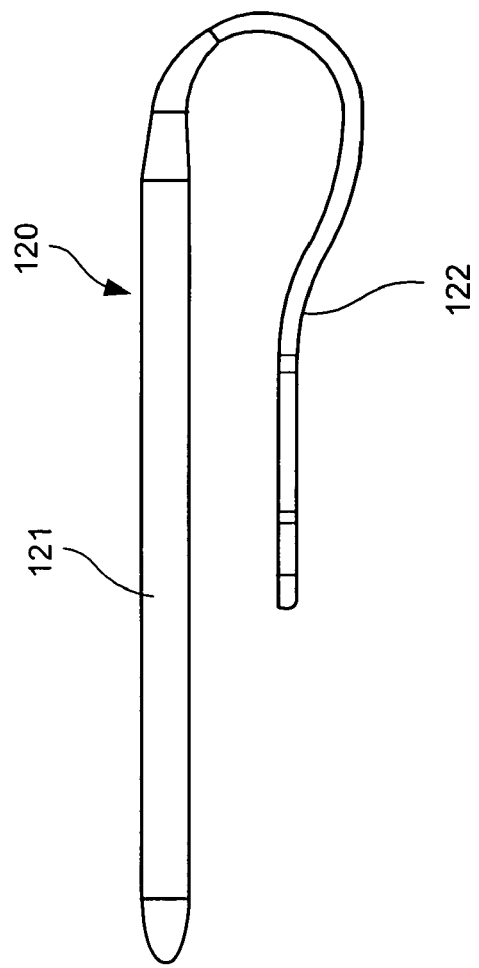
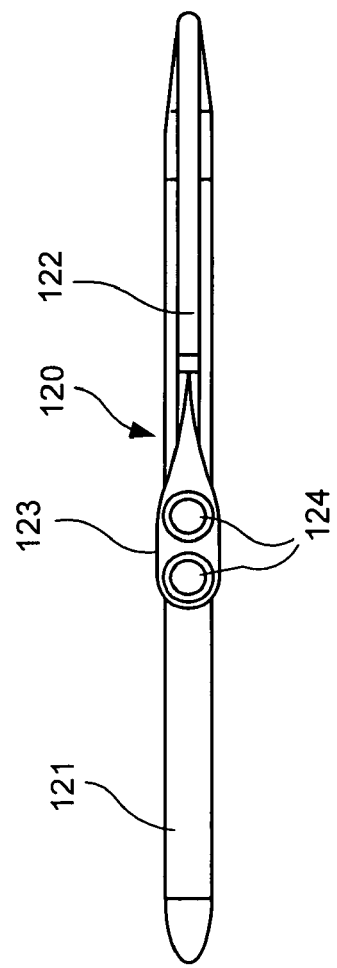

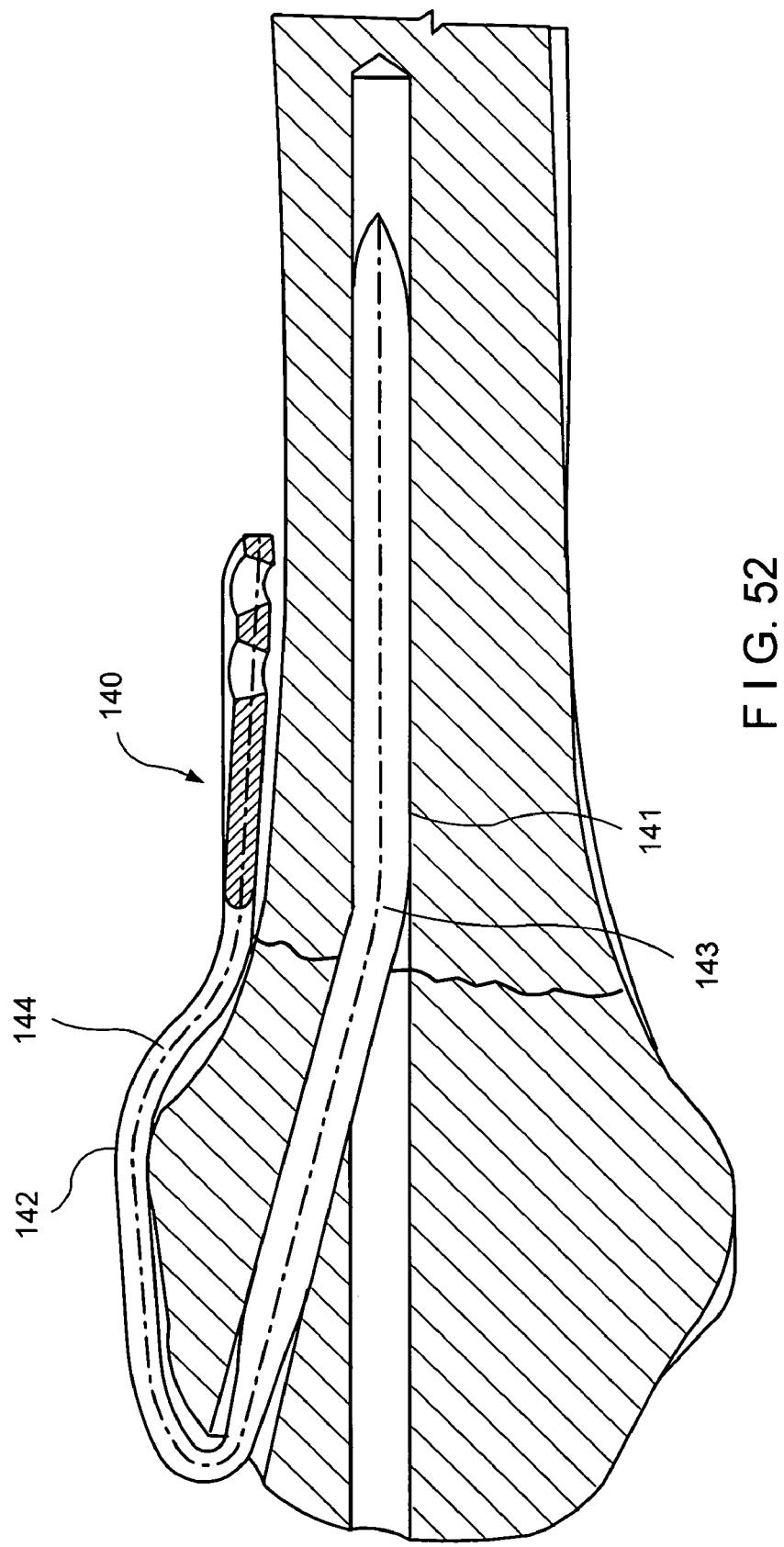
F I G. 52

IMPLANT DEVICE FOR APPLYING COMPRESSION ACROSS A FRACTURE SITE

CROSS RELATED APPLICATION

This application is a C-I-P of application Ser. No. 10/073, 826 filed Feb. 11, 2002, now U.S. Pat. No. 7,037,308 which claims the benefit of Provisional Application Ser. No. 60/268, 099 filed Feb. 12, 2001.

FIELD OF THE INVENTION

The invention relates to an implant device for applying compression across a fracture site in a bone and in particular to such an implant device which is constructed as a wire element which is used without separate pins.

BACKGROUND AND PRIOR ART

By way of example, fractures of the olecranon (upper end of the ulna at the level of the elbow) and fractures of the patella (kneecap) are fractures that involve an articular surface. Restoration of the joint surface to anatomic alignment is the accepted method of fixation.

Both the olecranon and patella are loaded during joint flexion. The deep articular surface is loaded in longitudinal compression by the reactive forces across the articular surface; the superficial bone surface is loaded in tension by the pull of a strong muscular insertion (the triceps in the case of the olecranon, and the quadriceps tendon in the case of the patella). As a result, these bones normally have a compressive side (deep surface) and a tension side (superficial surface).

A well accepted method of fixation of both olecranon fractures and patella fractures is a technique known as FIG. 8 tension band wiring. FIGS. 1 and 2 show an example of the known technique. Referring to these figures, two stiff stainless steel pins A are driven longitudinally into bone B across the fracture site C. Instead of pins, screws can be utilized. A flexible wire D is passed through a drill hole E on one side of the fracture site C and the two ends of the wire are crossed over the fracture site to the opposite side. One wire is then passed under the ends F of the two pins A, and the wire twisted and tightened at G to the other end to develop tension in the wire to produce compression across the fracture site.

The tension band technique holds the tension side of the bone in apposition. Since the deep surface is under load from the articular surface, the technique results in production of compressive force across the fracture site, resulting in secure fixation, promoting early union of the fracture and early motion of the joint.

One problem with this standard FIG. 8 tension band wiring occurs because standard large pins A are used which protrude from the end of the bone at F at the location where a major tendon inserts. Because of this, the ends F of the pins frequently cause irritation of the soft tissues and require removal.

A minor technical problem with the standard FIG. 8 tension band wiring is that the passage of the wire through drill hole D and through the tendon and under the pins can be cumbersome.

Another problem with standard FIG. 8 tension band wiring is that there is no physical connection between the stiff intramedullary pin and the extraosseous wire. As a result, this construct has little resistance to rotation at the fracture site.

SUMMARY OF THE INVENTION

An object of the invention is to provide an implant device which overcomes the above problems and disadvantages by avoiding the use of the stiff pins that may protrude from the bone and providing a continuous length of wire to apply the compressive force across the fracture site.

The above and further objects of the invention are achieved by an implant device which comprises a structural form having a first portion adapted to be implanted into a bone across a fracture site in the bone, and a second portion integrally formed with the first portion and extending outside the bone for passing on a superficial surface of the bone such that the first and second portions are juxtaposed with one another, and a fixation element adapted to be secured to the bone, for cooperating with the second portion of the structural form to maintain tension force in the second portion for producing compression of the bone across the fracture site.

In a particular embodiment, a tensioning device is engageable with said fixation element and with said second portion to develop said tension force.

Another object of the invention is to provide a simplified embodiment which is reliable, easy to manufacture and avoids the use of washers to secure the fixation element to the implant.

In accordance with this object, the implant is directly secured to the bone by the fixation element when the implant is in tension and applies compression across the fracture.

In the simplified embodiment of the invention, the first and second portions of the implant are formed by respective first and second legs joined by a bend portion wherein the first leg is dimensional and configured to be embedded in the bone and the second leg extends extraosseously on the superficial surface of the bone. By applying a pulling force on the second leg to develop tension in the implant, the second leg can then be directly secured to the bone to maintain the tension and apply compression across the fracture.

In accordance with the invention, the implant is formed from a single piece of material bent in loop form to provide the first and second legs joined by the bend.

In further accordance with the invention, the second leg has a flat or slightly curved lower surface secured to the bone by the fixation element, directly and without a washer.

In further accordance with the invention, the bend portion has a small enough cross-section to facilitate bending of the implant while providing resilience of the implant at the bend.

BRIEF DESCRIPTION OF THE FIGURES OF THE DRAWING

FIG. 11 is an elevational view of a different embodiment of the tensioning device in a relaxed state.

FIG. 13 is a sectional view taken along line 13-13 in FIG. 11.

FIG. 15 is a plan view illustrating a further embodiment of the invention.

FIG. 15A is a plan view of a modification of the embodiment illustrated in FIG. 15.

FIG. 16 is a side elevational view of the embodiment illustrated in FIG. 15.

FIG. 17 is a top plan view showing the embodiment of FIG. 15 installed in the bone.

FIG. 17A is similar to FIG. 17 but illustrates the modification in FIG. 15A.

FIG. 18 is a side elevational view showing the embodiment of FIG. 15 installed in the bone.

FIG. 19 is a top plan view of a further embodiment of the invention.

FIG. 20 is a side elevational view of the embodiment in FIG. 19.

FIG. 21 is an end view as seen in the direction of arrow X in FIG. 19.

FIG. 22 is a sectional view taking on line 22-22 in FIG. 20.

FIG. 23 is a side elevational view showing the embodiment of FIG. 19 installed in the bone.

FIG. 24 is a top plan view of FIG. 23.

FIG. 25 is a sectional view taking along line 25-25 in FIG. 23.

FIG. 30 is a plan view of a further embodiment of the invention shown installed in the bone.

FIG. 31 is an elevational view of FIG. 30.

FIG. 36 is a top plan view of another embodiment of a fixation device according to the invention.

FIG. 37 is a side elevational view thereof.

FIG. 41 shows the installation of the fixation device in elevational view.

FIG. 42 is a perspective view of another embodiment of the implant adapted for fixation of fractures of the distal radius.

FIG. 43 is a top plan view of FIG. 42.

FIG. 48 is a top plan view of a modified embodiment showing its method of manufacture.

FIG. 49 is a sectional view taken along 49-49 in FIG. 48.

FIG. 50 is a side view of the completed embodiment of FIG. 48.

FIG. 51 is a top view of FIG. 50.

FIG. 52 is a side view of a modified embodiment of the implant.

DETAILED DESCRIPTION

The drawings illustrate a fracture fixation implant device 1 for applying compression across a fracture 2 in a bone B. The bone B, for example, may be the olecranon or the patella that involve an articular surface.

Figure 1:
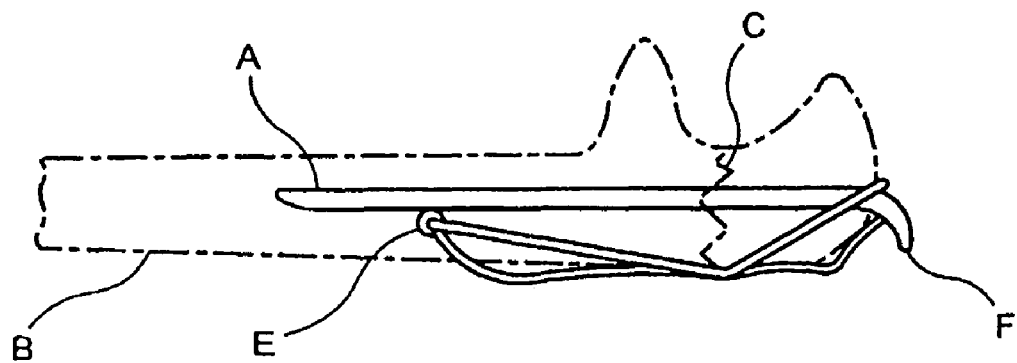
FIG. 1 is a side view of a conventional fixation device.
Figure 2:
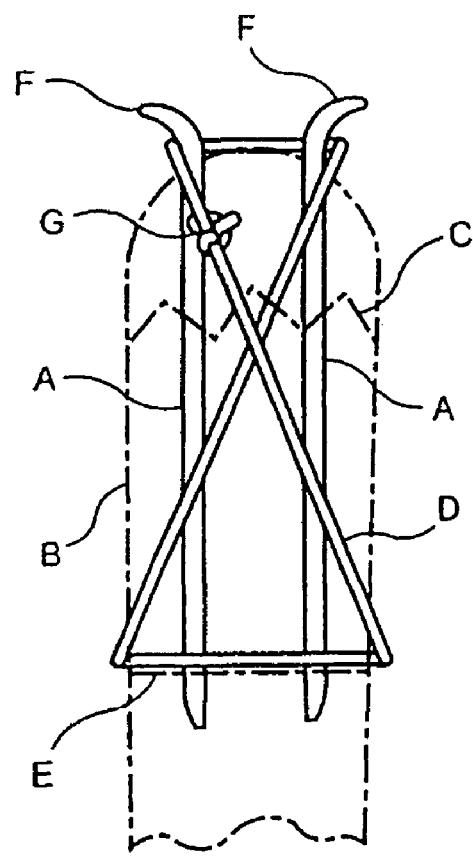
FIG. 2 is a plan view, from below at the posterior side in FIG. 1.
Figure 3:
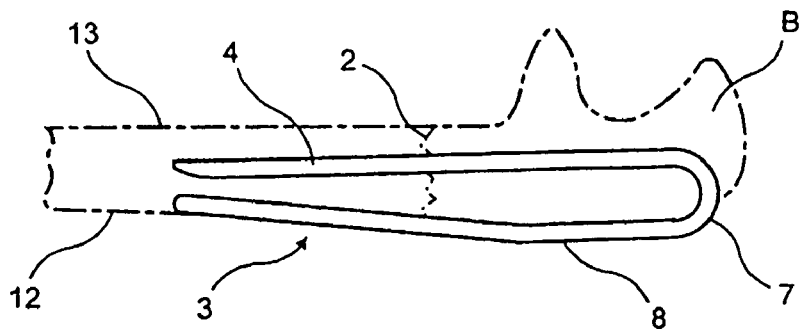
FIG. 3 is a side view of the fixation device of the invention implanted in a bone.

The implant device 1 comprises a continuous wire element 3 formed with two spaced longitudinally extending legs 4 which are adapted to be driven into the bone B across the fracture 2. The term "wire" or "wire element" is an art recognized term and covers elements having circular or rectangular cross-sections and commonly referred to as pins, wires or bars. The legs 4 form a first portion 5 of the wire element and the legs 4 extend at their ends remote from free ends 6 thereof to bend portions 7 extending outside the bone. Integrally connected to bend portions 7 is a second portion 8 extending backwardly from the bend portions 7 in juxtaposition with the legs 4 of the first portion 5. The second portion 8 includes legs 9 continuous with respective bend portions 7 and crossing one another at an intersection 10 which is located approximately at the fracture 2. The legs 9 extend to a connecting portion 11 in the form of a U-shaped bend to complete the continuity of the wire element 3. In FIG. 3 the wire element 3 is illustrated in an embedded condition in the bone so that the second portion 8 extends on a lower or posterior surface 12 of the bone.

Figure 4:
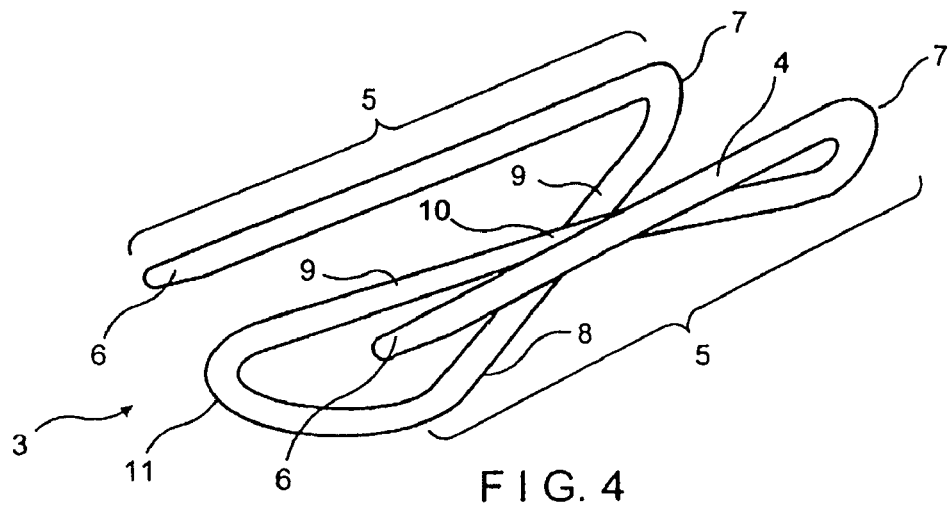
FIG. 4 is a perspective view of one embodiment of the fixation device.
Figure 4A:
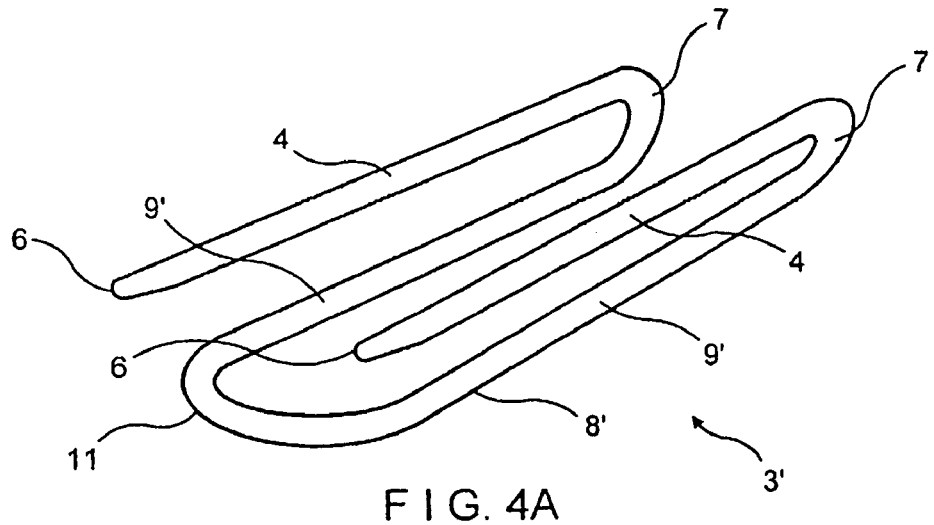
FIG. 4A is a perspective view of another embodiment of the fixation device.

FIG. 4A illustrates a modified embodiment of the wire element in which the same numerals are used to designate the same parts and primes are used for modified parts. In FIG. 4A, the wire element 3' has legs 9' of the second portion 8' which do not cross one another as in FIG. 4 but are spaced from one another. In other respects, the wire element 3' is the same as wire element 3 in FIG. 4.

Hereafter, the invention will be described with reference to the wire element 3 of FIG. 4, but it is to be understood that the wire element 3' could also be used.

Figure 7:
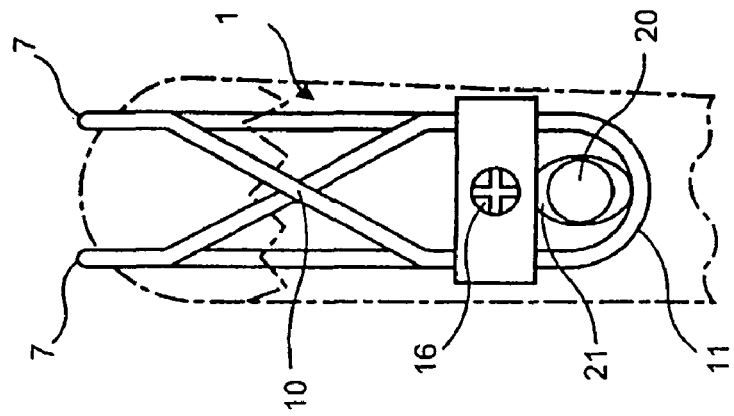
FIG. 7 shows application of tension force by the tensioning device.
Figure 6:
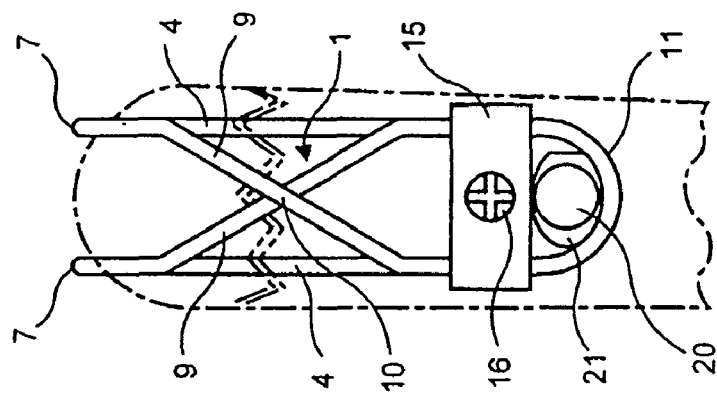
FIG. 6 shows the device of FIG. 5 with a tensioning device prior to application of tension force.
Figure 5:
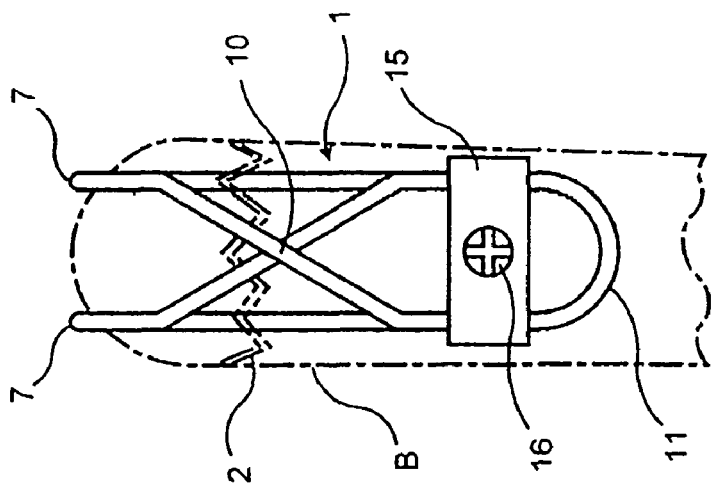
FIG. 5 is a plan view of the fixation device at the posterior side.

A washer 15 is secured at the posterior surface 12 of the bone by a bone screw 16. The legs 9 are loosely disposed below the washer 15. A tensioning device 20 is then installed between the washer 15 and the bend portion 11 of the wire element 3. The tensioning device 20 includes a rotatable cam 21 temporarily installed in the bone. In the position shown in FIG. 6, the cam does not apply any tension to the wire element 3. When the cam is turned from the position shown in FIG. 6, a force is applied to the U-shaped bend 11 which develops tension in the wire element and causes the bend portions 7 to bear tightly against the distal end of the bone and produce compression across the fracture 2. In the ninety degree position shown in FIG. 7 of the cam 21, a maximum compression is developed across the fracture 2. When the proper tension has been developed in the wire element, the washer which has been loosely seated by the bone screw 16 is then fully seated by tightening the bone screw 16. Thereby, the tension in the wire element is maintained. The cam 21 which has been temporarily installed in the bone is then removed.

Figure 8:
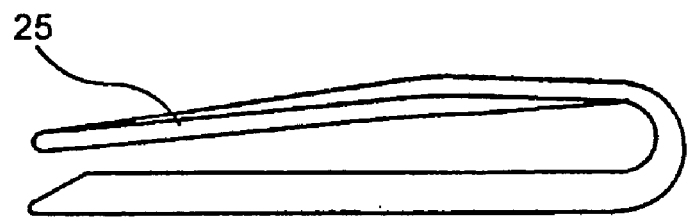
FIG. 8 is a side view of a modified embodiment of the fixation device in which the wires are crossed at the upper or superior surface of the bone.
Figure 9:
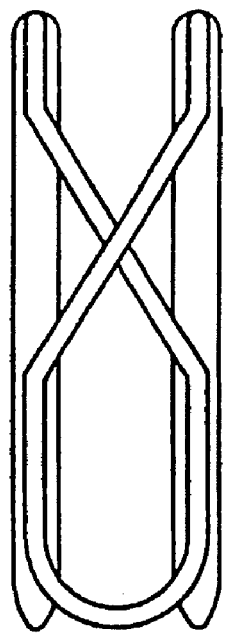
FIG. 9 is a top plan view of the device in FIG. 8.
Figure 10:
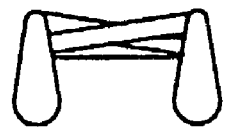
FIG. 10 is an end view of the device in FIG. 8.
Figure 14:
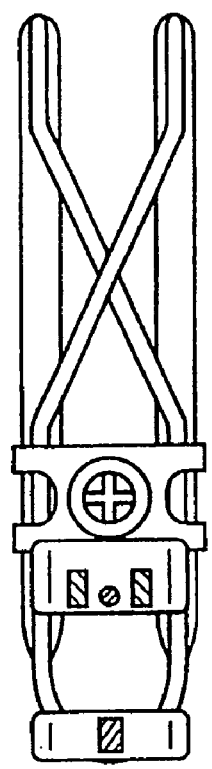
FIG. 14 is a sectional view taken along line 14-14 in FIG. 11.

FIGS. 8-10 are similar to the embodiment of FIGS. 3-7 except that the second portion 8 with the legs 9 or 9' is adapted to extend on the upper or anterior surface of the bone and tensioning of the wire element takes place at the upper surface. In practice, the legs 9 or 9' can be positioned on any superficial surface of the bone.

The installation of the implant is carried out as follows.

Two holes are drilled at the end of the bone at a spacing corresponding to the width of the implant as measured by the spacing of the legs 4 of the implant device thereof. The legs 4 of the implant device are impacted longitudinally into the drilled holes entering and aligning to the medullary canal. The fracture site is closed and the implant device is firmly seated and secured with the bone screw and washer to the bone at one end of the implant device. Compression at the fracture is achieved by turning the cam between the washer and the U-shaped bend of the implant device to effect further compression whereafter the screw is fully tightened and the washer is seated and then the cam is removed. In lieu of the cam, the tension force in the wire element can be produced by the surgeon applying pressure to the U-shaped bend portion 11 and then tightening the bone screw 16 while the wire is under tension.

Implant devices having wire elements of different diameter are suited for different bone fractures. For example, a 0.062 inch diameter wire can be used for olecranon fractures whereas a larger diameter wire would be used for patella fractures and a smaller diameter wire element would be used for transverse lateral or medial malleolar fractures.

In accordance with a particular feature of the invention, the diameter of the wire of the continuous wire element need not be uniform along its length and it is particularly advantageous if the legs 4 of the wire element are of greater diameter than the remainder of the wire element in the legs 9 or 9' and U-shaped bend 11 of the second portion 8 or 8'. In this way, absolute reliability of the embedded legs 4 of the first portion is obtained while flexibility of the wire element of the second portion can be obtained to achieve development of adequate tension in the wire element and resulting compression across the fracture.

Figure 12:
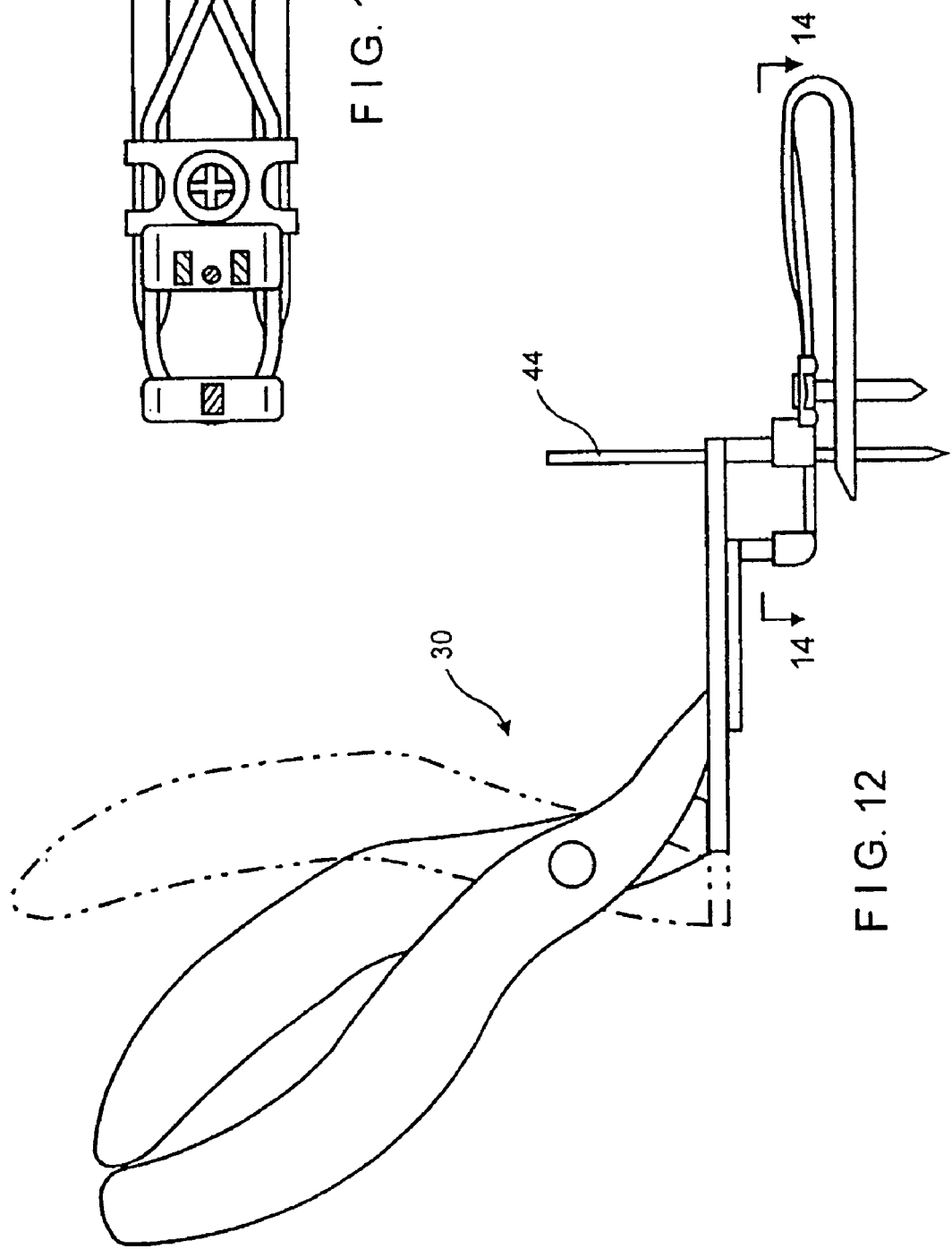
FIG. 12 shows the tensioning device of FIG. 11 in an active state in which tension is applied to the fixation device.

FIGS. 11-14 show another embodiment of the tensioning device designated generally by numeral 30. The tensioning device 30 comprises lever arms 31 and 32 connected together by a hinge 33. The arms 31 and 32 have respective hand-engaging gripper ends 34 and 35 above the hinge 33 and actuator arms 36 and 37 below hinge 33. The arm 36 supports an actuating jaw 38 at its lower end and the arm 37 supports a counter-bearing jaw 39 at its lower end. The jaws 38 and 39 are slidable with respect to one another and jaw 38 can be moved from an inactive state, as shown in FIG. 11 in which the wire element is not subjected to tensile stress by the tensioning device, to active state as shown in FIG. 12 in which the jaw 38 has been displaced to apply tension to the wire element. The jaw 39 is connected by a strut 40 to an actuator plate 41 and the jaw 38 is connected by struts 42 to a counter-bearing plate 43. The counter-bearing plate 43 can be secured by a temporary pin 44 which is placed in a drill hole in the bone. The U-shaped bend 11 of the second portion 8 of the wire element, passes around a back surface of the actuator plate 41. When the lever arms 34 and 35 are brought together as shown in FIG. 12, the actuator plate 41 is displaced away from the counter-bearing plate 43 to produce tension in the wire element. When the desired degree of tension has been achieved, the bone screw 16 is fully tightened, the pin 44 is extracted and the tensioning device is removed.

Although the prior figures have depicted an implant with two separate legs for both the first portion 5 and the second portion 8, either the first portion 5 or the second portion 8 or both may consist of one leg or more than two legs Referring to FIGS. 15 and 16, therein is shown a further embodiment of a fixation device 103 according to the invention in which the first portion consists of a single leg. The fixation device 103 has a leg 104 adapted for insertion into the bone and the leg 104 extends to a bend 107 connected to one leg 109 of the second portion 108 of the device. A U shaped bend 111 connects leg 109 with a second leg 109 of the second portion 108. FIGS. 17 and 18 illustrate the installation of the fixation device 103 in bone B. As seen therein, the leg 104 is driven into the bone and extends across the fracture 102 and the second portion 108 consisting of legs 109 extends on an outer surface of the bone. The legs 109 of the second portion are secured to the bone by a bone screw 116 installed in a washer 115, following the development of tension in the device in a manner previously explained.

FIGS. 15A and 17A illustrate a modification of the embodiment illustrated in FIGS. 15 and 17. Herein, the fixation device is comprised of two parts 63 each having a leg 64 adapted to be implanted into the bone to form fixation portion 65. The leg 64 is connected by a bend 67 to second leg 69 of second portion 68 which extends backwardly and is juxtaposed with leg 64. The second legs 69 of the two parts 63 can be pulled to fix the fracture and develop tension in parts 63 and apply compression across the fracture. Washer 75 is secured to the bone by bone screw 76 to connect the second legs 69 together and maintain the tension developed in the two parts 63 via the second legs 69.

FIGS. 19 through 25 illustrate another embodiment of the fixation device according to the invention which is particularly applicable to the fixation of a fracture of the olecranon. This embodiment is distinguished from the earlier described embodiments in that the second portion 208 is non-planar but is bent in more than one plane to match the contour of the bone as shown with particularity in FIG. 25. In particular, the fixation device comprises two legs 204 which are driven into the intramedullary canal across the fracture 202. The legs 204 extend to the bend portions 207 which extend out of the bone to the second portion 208 which comprises the crossed legs 209 connected together by the U-shaped bend 211. It is noted that the U-shaped bend 211 is not composed only of curved portions but includes a straight portion with end radii connecting the U-shaped bend 211 to the legs 209 of the second portion 208. When reference is made in this disclosure to the U-shaped bend, this not only includes curved portions but portions which can be straight and includes such configurations as V-shaped bends and the like. The legs 209 of the second portion 208 have a transition region 220 in which the legs are bent out of plane and pass in opposition at the sides of the bone as shown in FIG. 25. The U-shaped bend 211 extends out of plane and connects the ends of the legs 209 as shown in FIGS. 22 and 25. The legs 204 are formed with a larger diameter than the legs 209 and there is a gradual taper in diameter between the legs at the bend portions 207. As evident from FIG. 25, the U-shaped bend 211 which is curved in two planes engages the surface of the bone B and forms a stabilized engagement therewith.

Figure 26:
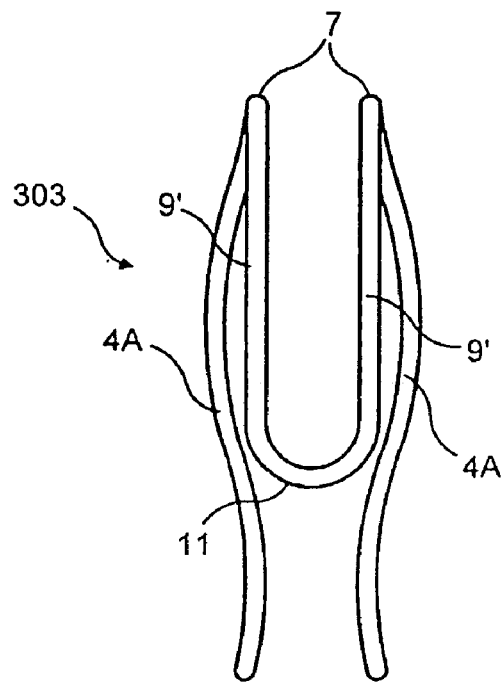
FIG. 26 is a plan view of a further embodiment according to the invention.
Figure 27:
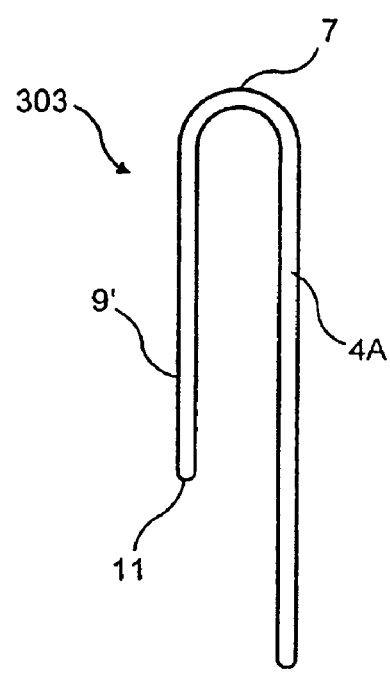
FIG. 27 is a side elevational view of the embodiment shown in FIG. 26.

FIGS. 26 and 27 show another embodiment of the fixation device designated 303 which is similar to the embodiment shown in FIG. 4A. The same reference numerals will be used to designate the same parts. The fixation device 303 is particularly applicable for fractures at the distal end of the ulna which is often fractured in addition to fractures of the distal radius. In this embodiment, the diameter of the wire elements is constant throughout and the characterizing feature is that the legs 4A which are inserted into the bone (the ulna) are not linear but have a curved or bent shape to produce a resilient effect when inserted into the intramedullary canal to produce greater fixation of the bone from the interior and help prevent the device from rotating due to resilient engagement of the legs 4A within the intramedullary canal. In use, the free ends of the legs 4A of the fixation device 303 are inserted into the intramedullary canal and squeezed together so that upon further insertion the more widely spaced bend portions of the legs 4A are squeeze more tightly and secure the fixation device with resilient pressure against the inner wall of the intramedullary canal.

Figure 28:
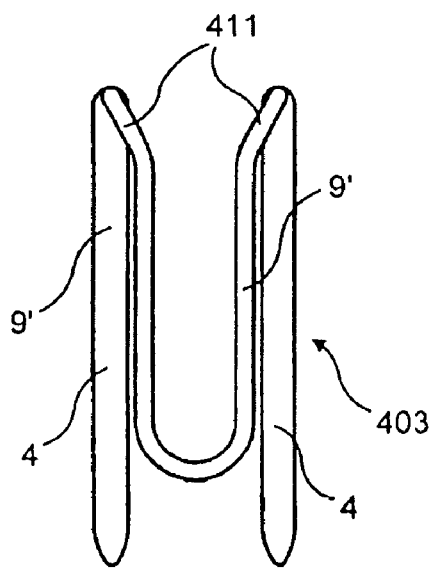
FIG. 28 is a plan view of a further embodiment according to the invention.
Figure 29:
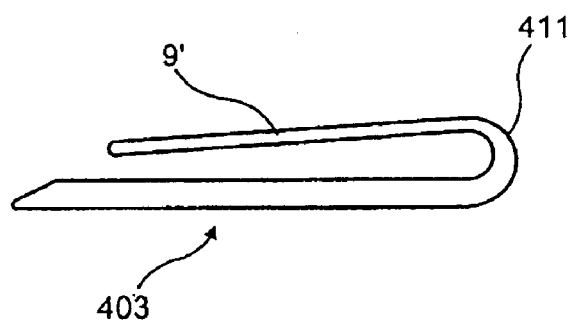
FIG. 29 is a side elevational view of the embodiment illustrated in FIG. 28.

FIGS. 28 and 29 show another embodiment 403 of the fixation device which is similar to the embodiment in FIG. 4A and the embodiment in FIGS. 26 and 27. The fixation embodiment 403 in FIGS. 28 and 29 is particularly adapted to fractures of the patella. The fixation device 403 differs from that in FIG. 4A in that bend portions 411 connecting the legs 4 and 9' are not in the same plane as the legs 9' so that the spacing between the opposite legs 9' is less than that between the opposite legs 4 as evident from FIG. 28. Additionally, the diameter of the legs 4 is greater than the diameter of the legs 9' and the change in diameter takes place gradually through the bend portions 411. Referring to FIGS. 30 and 31, therein the fixation device 403 is shown implanted in the patellar bone 2 across the fracture 2 in which two washers 15 and two bone screws 16 are employed.

Figure 32:
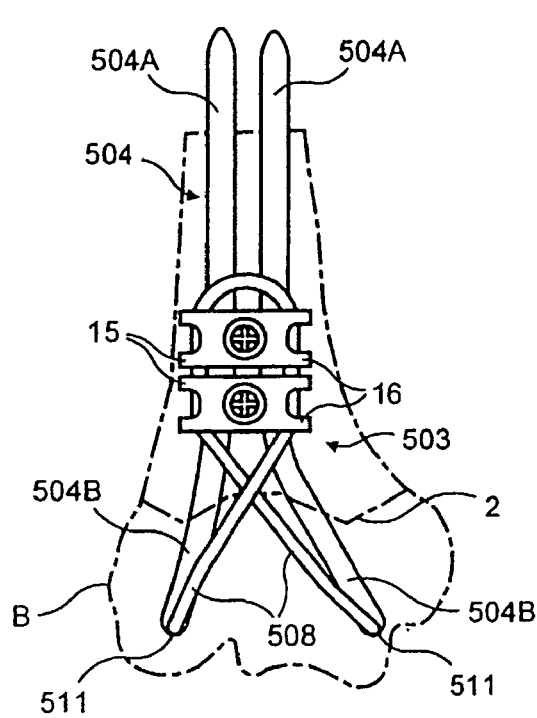
FIG. 32 shows a further embodiment of the invention installed in the bone.
Figure 33:
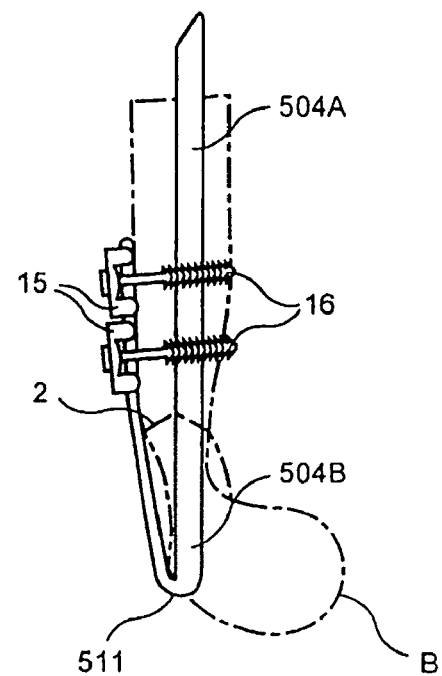
FIG. 33 is an elevational view of FIG. 32.

FIGS. 32 and 33 show another embodiment of the invention similar to the embodiment in FIG. 4 but modified to provide fixation for fractures of the proximal humerus, the distal humerus, the lateral humerus, the lateral malleolus and medial malleolus. The embodiment illustrated in FIGS. 32 and 33 and designated 504 differs from the earlier described embodiment of FIG. 4 in that legs 504 of the fixation device are not straight but are formed with straight portions 504A and diverging non-symmetrical portions 504B. The implant thereby is adapted to the configuration of the particular bone and the relatively wide aspect or spacing of the bend portions 511 as shown in FIG. 32. In this embodiment, two washers 15 and the bone screws 16 are utilized as in previous embodiments.

Figure 34:
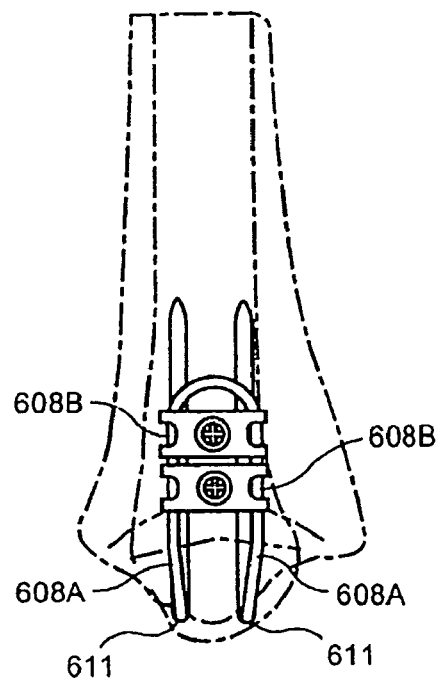
FIG. 34 shows a further embodiment installed in the bone.

FIG. 34 shows a variation of the embodiment in FIG. 32 adapted for being implanted in the medial malleolus. In this embodiment instead of the legs of the implanted first portion 5 being non-parallel, the legs 604 are parallel and the legs of the second portion are bent and widen from the bend portions 611 to form diverging leg portions 608A which merge with parallel leg portions 608B.

Figure 35:
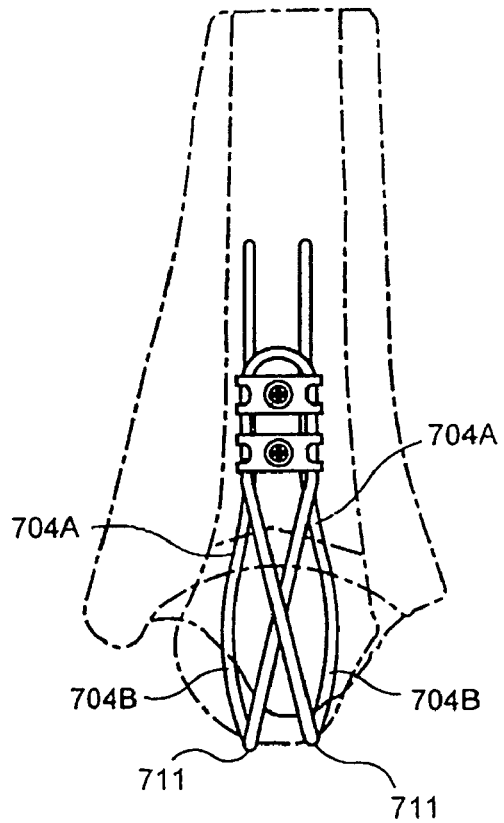
FIG. 35 is a plan view showing a further embodiment installed in the bone.
Figure 40:
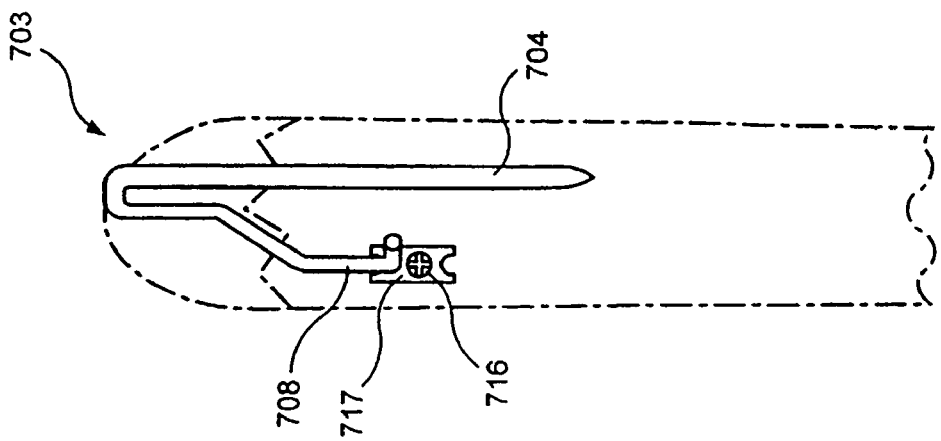
FIG. 40 shows the installation of the fixation device in top plan view.

In a modification shown in FIG. 35, the legs of the first portion include diverging portions 704A which then converge to portions 704B which are joined to bend portions 711 connected to the crossing legs of the second portion of the fixation device.

FIGS. 36 and 37 show another embodiment of a fixation device 703 having a single straight leg 704 forming the first portion 705 of the fixation device connected by a bend portion 711 to a single leg 709 forming the second portion 708 of the fixation device. At the end of leg 709, a 90° bend is formed to define a hook 710.

Figure 39:
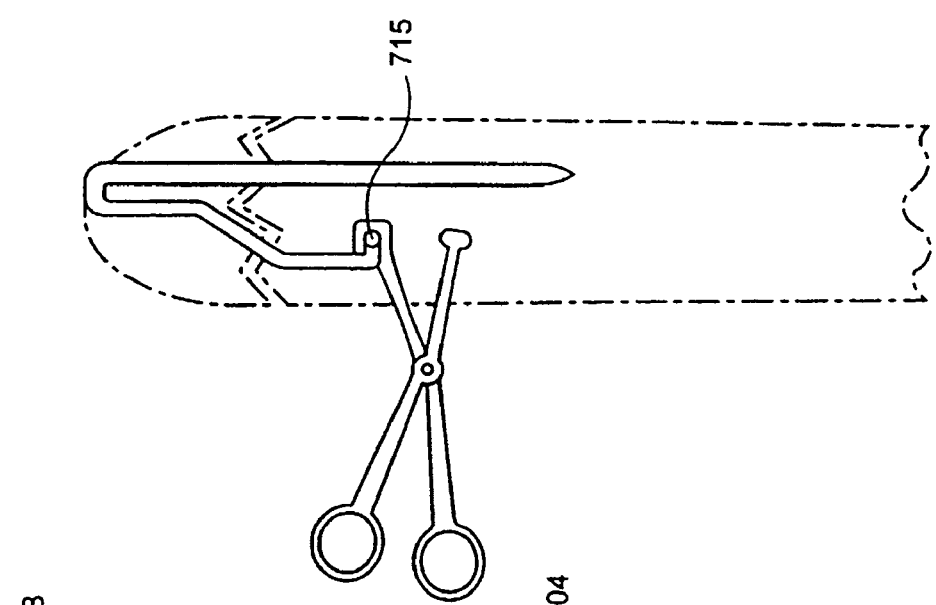
FIGS. 38 and 39 illustrate successive stages of installation of the fixation device of FIG. 36.
Figure 38:
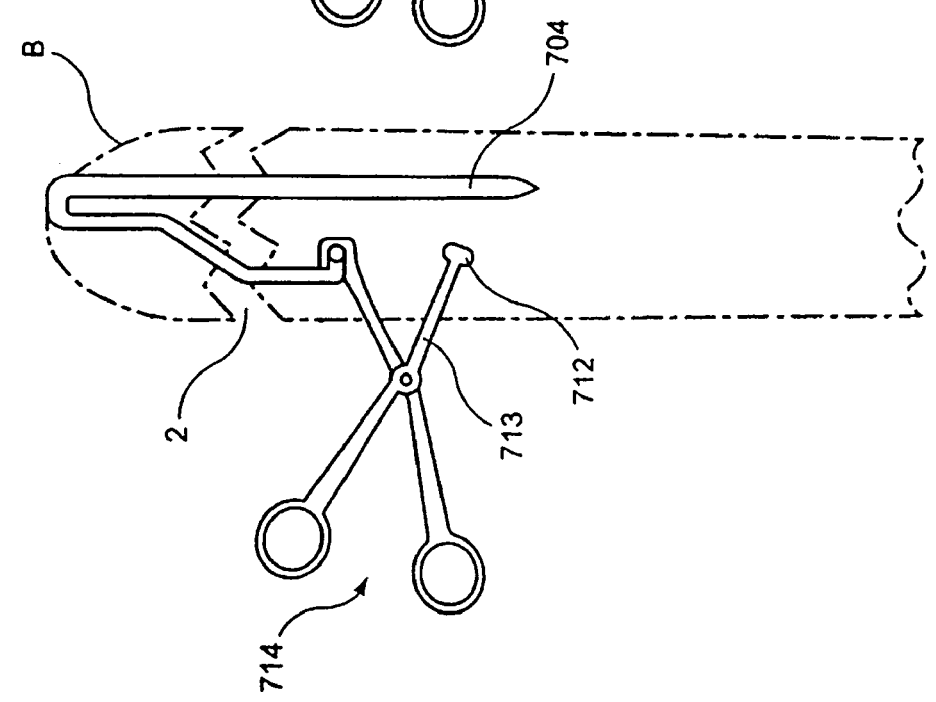

In FIG. 38, the leg 704 of the fixation device is impacted into the intramedullary canal of the bone B across the fracture 2. An arching hole 712 is drilled in the bone B and is engaged by one arm 713 of a tensioning instrument 714. The other arm 715 engages the hook 710 at the end of leg 708. The tensioning instrument is then closed as shown in FIG. 39 to close and compress the fracture. A guide hole 715 is drilled in the bone B tensioning instrument 714 is then removed and hook 710 is impacted into the guide hole 715. A bone screw 716 and washer 717 is then installed to hold end of the leg 709 in place.

The embodiment shown in FIGS. 36-41 differs from the previously described embodiments in that instead of fixedly securing the end of leg 708 by the washer and bone screw, the hook which is impacted into the bone serves for anchoring the leg 708 and the bone screw and washer only serve for preventing the end of the leg from coming out of the bone. In the previously described embodiments the bone screw has to be tightened with substantial force to prevent the leg under the washer from sliding on the bone.

FIGS. 42-53 illustrate fracture fixation implants which are formed from a single piece of material which is bent in loop form to provide juxtaposed first and second legs joined by a bend.

Figure 44:
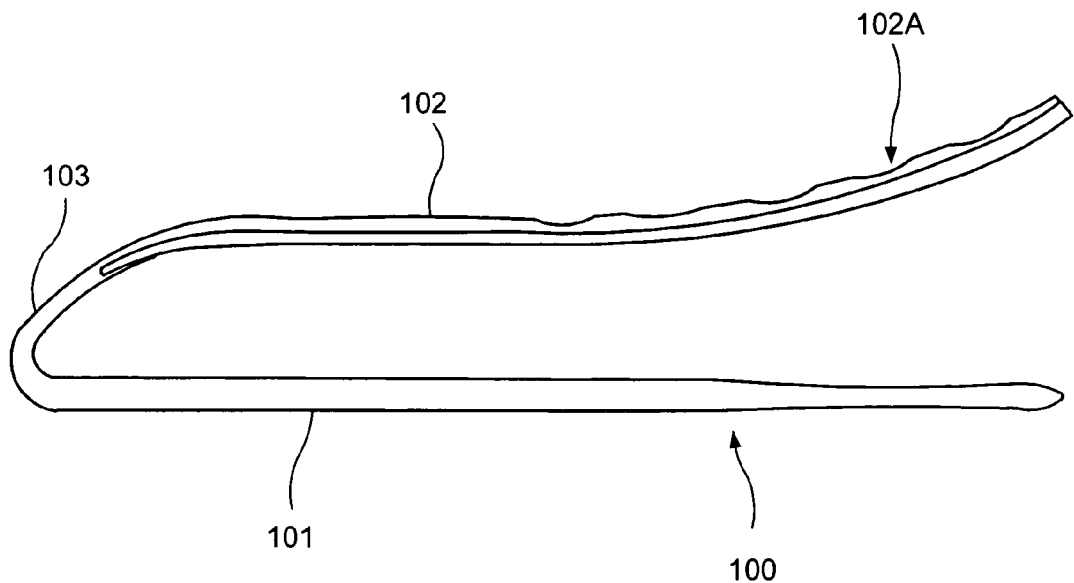
FIG. 44 is a side elevational view of FIG. 42.
Figure 45:
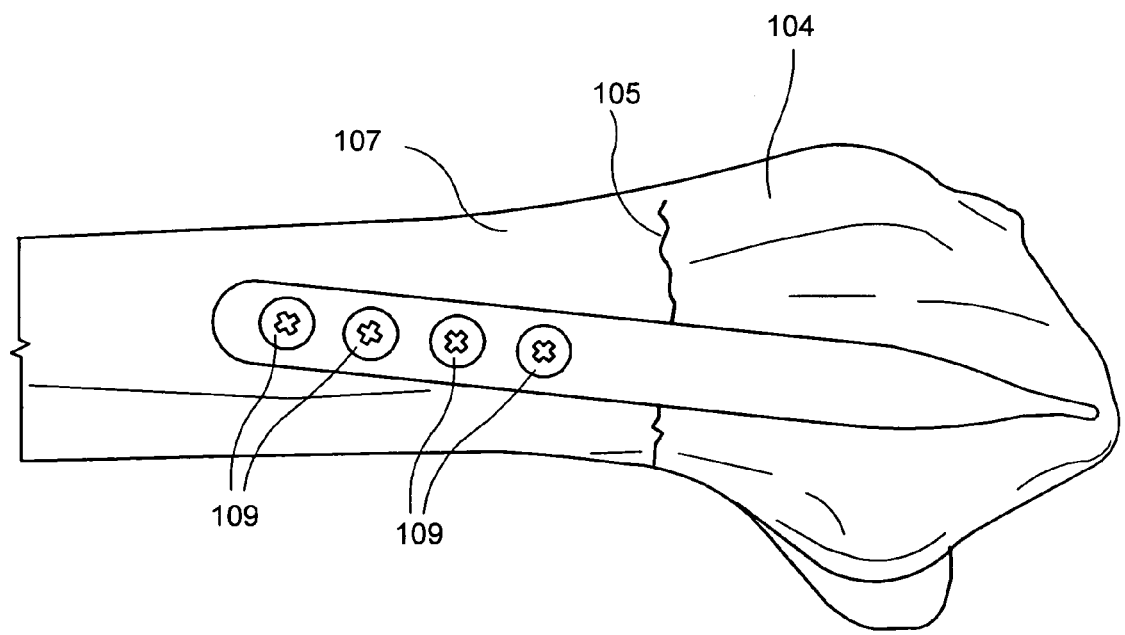
FIG. 45 is a top plan view showing fixation of a fracture of the distal radius with the implant of FIG. 42.
Figure 46:
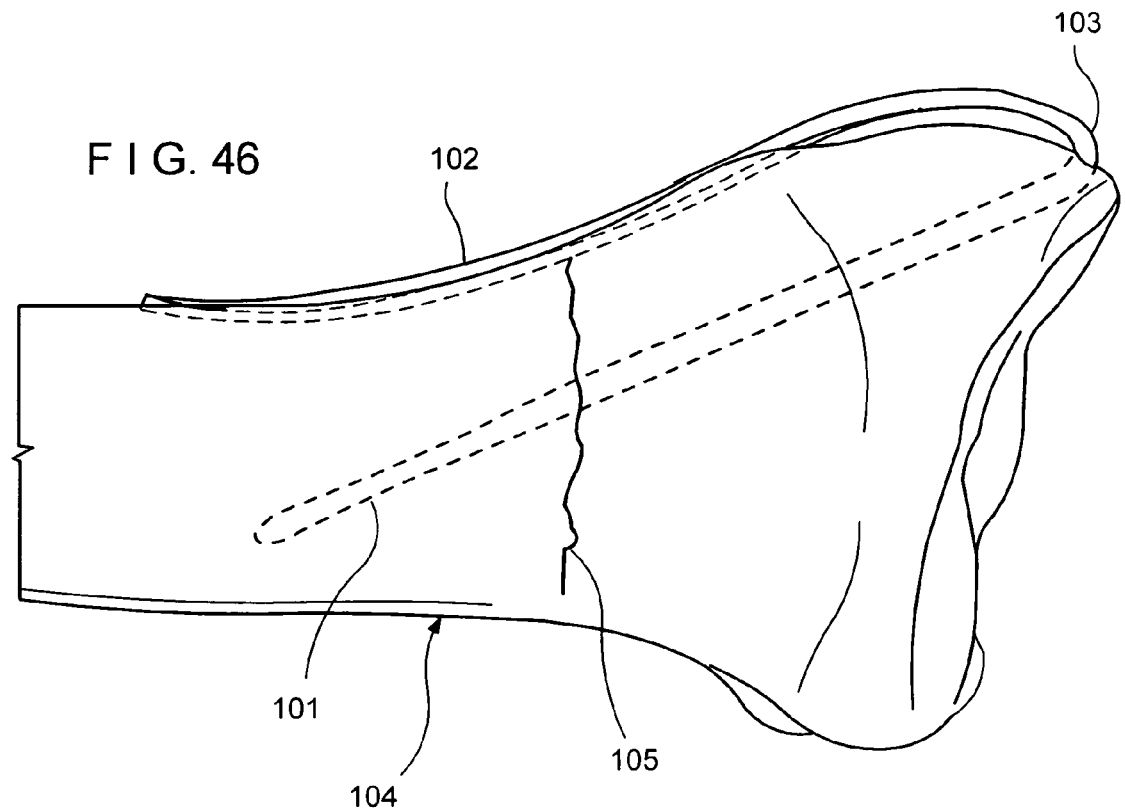
FIG. 46 is a side view of FIG. 45.

Referring to FIGS. 42-46 therein is shown an implant 100 having a first leg 101 joined to a second leg 102 by a bend 103. The first leg 101 is dimensioned and configured to be implanted within a bone 104, such as the distal radius as shown in FIGS. 45 and 46 to extend across a fracture 105 in the bone. Specifically, the first leg is of sufficient cross-sectional area to be embedded in the bone and provide sufficient frictional grip in the bone to be retained in the bone when tension is applied to the implant to produce compression across the fracture 105. The tip 106 of leg 101 can be tapered especially for large size legs, to facilitate entry of the leg 101 into the bone under a driving or impact force. The first leg 101 has a generally round cross-section which can vary in cross-sectional area along its length as shown in FIG. 44.

The second leg 102 extends backwardly from the bend 103 and leg 102 has a sufficient length to extend extraosseously on a superficial outer surface 107 of the bone across the fracture 105 whereby the implant 100 extends partly in the bone and partly out of the bone, the implant exiting from the bone at the bend. Thereby when a pulling force is applied to the leg 102, a compression will be developed across the fracture 105 in the bone. The leg 102 has a flat shape in the form of a plate and a plurality of holes 108 are provided in the plate in which fasteners, such as bone screws 109, can be directly installed in the bone to secure the second leg to the bone and maintain the compression across the fracture 105.

This embodiment is distinguished from the earlier described embodiments in that the implant does not require the use of washers to secure the implant to the bone.

The bend 103 is made of sufficiently small cross-sectional area to allow it to be bent and allow the leg 102 to be properly seated on the surface 107 of the bone. The end region 102A of leg 102 is slightly curved outwardly to match the bone contour.

As shown in FIGS. 42-44, the leg 101 preferably has a round cross-section and the bend 103 also preferably has a round cross-section. Although this is a preferred shape, it is also possible to provide polygonal cross sections as well.

The leg 102 transitions from the bend and has a relatively flat under surface which can be slightly curved or otherwise shaped to conform to the shape of the surface of the bone.

As shown in FIGS. 42-45, the bend 103 tapers in cross-sectional area between the first and second legs. The taper can be uniform or non-uniform. The bend must be formed of sufficiently small cross-sectional area to allow it to be bent and it forms a region of stress concentration.

Consequently, it is beneficial to taper it smoothly along a hyperbolic curve and not form any grooves or corners at which stress concentrations can develop. A region of smallest cross-sectional area 101 is preferably formed beyond the bend 103 in a transition region between the bend and the second leg so that should the implant fracture, this will take place in the region of smallest cross-section outside the bone where a repair can be made.

Figure 47:
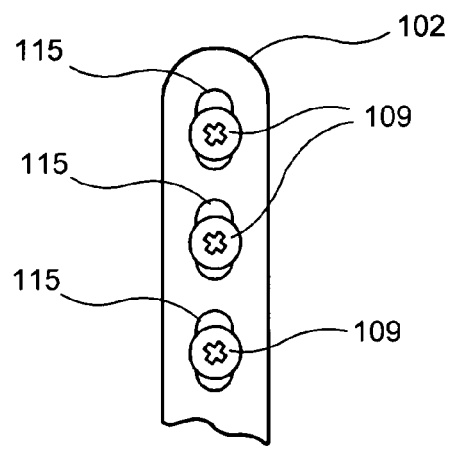
FIG. 47 is a top view of a modified arrangement of screw holes in the implant.

FIG. 47 shows a modified embodiment of the implant in which instead of round holes for screws 109, the holes are slotted as shown at 115 to provide longitudinal adjustment for the screws.

The embodiments in FIGS. 42-47 and those that follow hereafter are implanted without the need for a washer while providing the two legs that span the fracture both intramedullarly as well as extraosseously to obtain a tension in the implant and compression at the fracture (at the outer cortex) while the intramedullarly effect of the implanted leg 116 controls translation. This is the same effect as in the earlier embodiments of FIGS. 1-41 with the exception that requirement for the washer(s) is eliminated.

FIGS. 48-51 show the manner of manufacture of the implant.

In FIGS. 48-51 the implant is shown at 120 and is slightly modified from that of the embodiments shown in FIGS. 42-47 in that the second leg 122 is shown with a modified shape comprised of a wire-like portion with a platform 123 at its end which is slightly enlarged and is provided with only two holes 124 for bone screws. The leg 121 has a generally circular cross section which is greater than the cross-section of the second leg 122. In other embodiments, the first and second legs of the implant may be of equal diameter or even consist of a first leg that has a smaller diameter than the second leg.

The implant is manufactured as follows:

A piece of bar stock 130 is provided that has a diameter at least as great as the largest part of the implant. The material of the bar stock which is not a part of the final implant is removed. The sequence of manufacture is first to machine the surfaces at the end which is to form the second leg and then spin and grind down the remainder of the material to the dimensions in the other areas to form the finished implant. After completion of the formation of the finished implant, it is then bent to form the bend and produce the first and second legs in separated juxtaposition with one another as shown in FIGS. 50 and 51. In the particular embodiment shown in FIGS. 50 and 51 the bend has been formed with a large radius which provides a resilience or biasing effect of the second leg towards the first leg. The implant is now ready for installation at the fractured bone.

In addition, although FIGS. 42-51 show the implant to be of a predominantly uniplanar form, it is often optimal to provide additional bends in either the first leg, the second leg, or both, in order to conform to the anatomy of the site of fixation as well as provide additional rigidity to the form on the implant itself. For instance, the form of an implant for fixation of the lesser tuberosity of the shoulder may require additional bends in both the first leg to allow it to center in the intramedullary canal as well as in the second leg to allow this portion of the implant to conform to the anatomy of the bone in this region. These modifications do not affect the basic features of the invention as previously described.

Figure 53:
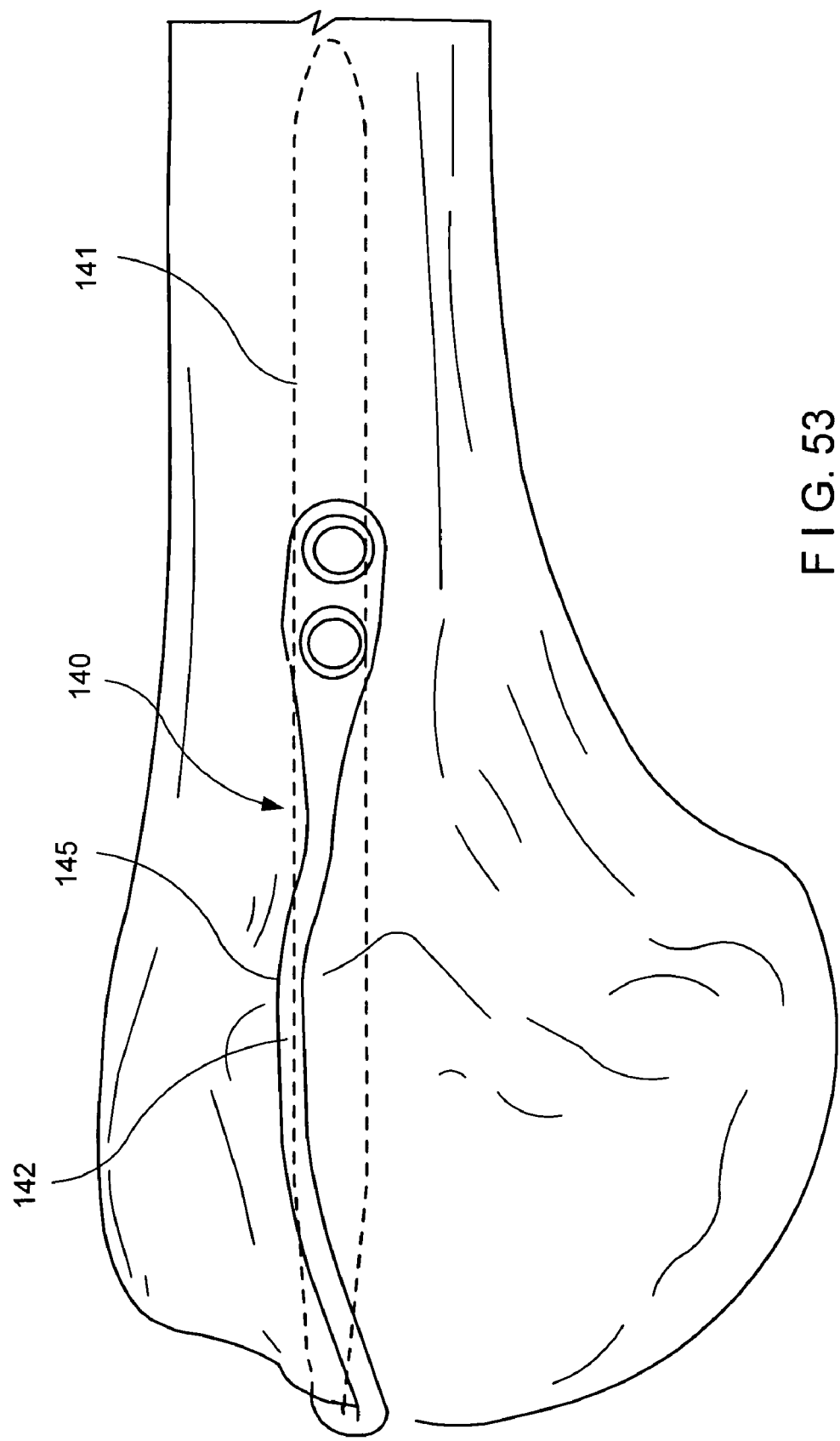
FIG. 53 is a top view of FIG. 52.

FIGS. 52 and 53 show a modified embodiment in which additional bends are provided. In these Figs., the implant is shown at 140 and legs 141 and 142 are provided with bends 143, 144 and 145 to enable the legs to conform to the anatomy.

Although the invention is disclosed with reference to particular embodiments thereof, it will become apparent to those skilled in the art that numerous modifications and variations can be made which will fall within the scope and spirit of the invention as defined by the attached claims.

The invention claimed is:

1. A fracture fixation implant comprising:
   a first portion constructed and arranged to be implanted within a bone across a fracture site in said bone,
   a second portion integrally formed with said first portion by a bend, said second portion being of a length to extend alongside but separated from said first portion across the fracture site outside the bone, said bend being of a size to extend outside the bone and space the second portion from the first portion by a distance so that the second portion can pass on a superficial surface of the bone, such that said first and second portions are juxtaposed with one another in offset planes with the first portion extending longitudinally in the bone and the second portion extending longitudinally on the outside of the bone, the arrangement being such that by applying a pulling force to said second portion, a tension force can be developed in said first and second portions, and
   a fixation element having means for being secured to said bone and for cooperating with said second portion to maintain said tension force developed in the first and second portions and produce compression of the bone across the fracture site,
   said first and second portions being integrally formed and joined together by said bend portion,
   said bend portion forming a transition between said first and second portions, said second portion transitioning to a surface adapted to conform with the superficial surface of the bone,
   said fixation element comprising a fastener which can pass through a hole in the second portion to secure the second portion directly to the bone at the superficial surface,
   said second portion comprising a flat body forming a plate in which said hole is provided to receive said fastener.

2. The implant of claim 1, wherein said second portion has a lower surface shaped to conform to the superficial surface of the bone.

3. The implant of claim 1, wherein the flat body of the second portion has a substantially uniform thickness.

4. The implant of claim 1, wherein at least one of said first and second portions has a non-uniform cross-sectional area.

5. The implant of claim 1, wherein said second portion has a cross-sectional area which is less than said first portion.

6. The implant of claim 5, wherein said flat body of said second portion has an end region wider than the rest of the implant.

7. The implant of claim 1, wherein said flat body of said second portion is provided with a plurality of said holes.

8. The implant of claim 1, wherein said first portion has a round cross section and a cross-wise area greater than that of said flat body of said second portion.

9. The implant of claim 8, wherein said first portion is substantially cylindrical.

10. The implant of claim 8, wherein said bend portion has a bend radius substantially greater than the distance between the juxtaposed first and second portions.

11. The implant of claim 7, wherein said holes are in the form of slots.

12. The implant of claim 1, wherein said second portion has a terminal end region which is curved outwards.

13. The implant of claim 1, wherein said first and second portions are formed from a single piece of material.

14. The implant of claim 1, wherein said second portion merges with said bend and has the smallest cross-sectional area of the implant beyond the bend to form a fracture zone.

15. The implant of claim 1, wherein said second portion is of sufficient length to extend across the fracture site.

16. The implant of claim 1, wherein said second portion includes a round portion connected at one end to said bend and at an opposite end merges with and changes cross-section with said flat body forming said plate.

17. The implant of claim 1, wherein said plate has a thickness less than that of the first portion.

18. The implant of claim 1, wherein the plate is substantially rectangular in cross-section.

19. The implant of claim 1, wherein said hole is drilled in said plate.

20. A fracture fixation implant comprising a single piece of material bent in loop form to provide juxtaposed first and second legs joined by a bend, said first leg being dimensioned and configured to be implanted within a bone to extend across a fracture in the bone, said second leg extending backwardly from said bend and having a length to extend on an outer surface of the bone across the fracture whereby the implant extends partly in the bone and partly out of the bone, the implant exiting from the bone at said bend, such that application of a pulling force on said second leg produces compression across the fracture in the bone, said second leg comprising a flat body forming a plat in which at least one hole is provided to receive a bone screw to directly secure the second leg to the bone and maintain the compression across the fracture.

21. The implant of claim 20, wherein said first leg has a round cross-section.

22. The implant of claim 20, wherein said bend has a round cross-section which is smaller in cross-wise area than said first leg.

23. The implant of claim 20, wherein said at least one hole is in the form of a slot.

24. The implant of claim 20, wherein said at least one hole is in a relatively flat part of the second leg and the bone screw directly secures the second leg to the bone without a washer.

25. The implant of claim 20, wherein said second leg includes a round leg connected at one end to said bend and at an opposite end merges with and changes cross-section with said flat body forming said plate.

26. The implant of claim 20, wherein said plate has a thickness less than that of the first portion.

27. The implant of claim 20, wherein the plate is substantially rectangular in cross-section.

28. The implant of claim 20, wherein said hole is drilled in said plate.

29. A fracture fixation implant comprising a single piece of material bent in loop form to provide juxtaposed first and second legs joined by a bend, said first leg being dimensional and configured to be implanted within a bone to extend across a fracture in the bone, said second leg extending backwardly from said bend and having a length to extend on an outer surface of the bone across the fracture whereby the implant extends partly in the bone and partly out of the bone, the implant exiting from the bone at said bend, such that application of a pulling force on said second leg produces compression across the fracture in the bone, said second leg being provided with at least one hole in which a bone screw can be installed to directly secure the second leg to the bone and maintain the compression across the fracture; wherein the method of forming said implant comprises the steps of
providing bar stock of a size greater than the size of said first and second legs,
removing material from the bar stock to form said second leg with a relatively flat portion, the first leg with a shape and dimension for implanting in the bone and a portion connecting the first and second legs destined to form the bend, and bending the latter said portion to form said bend.

30. The method of claim 29, comprising forming a plurality of said holes in said second leg.

31. A fracture fixation implant comprising:
a first portion constructed and arranged to be implanted within a bone across a fracture site in said bone,
a second portion integrally formed with said first portion by a bend, said second portion being of a length to extend alongside but separated from said first portion across the fracture site outside the bone, said bend being of a size to extend outside the bone and space the second portion from the first portion by a distance so that the second portion can pass on a superficial surface of the bone, such that said first and second portions are juxtaposed with one another in offset planes with the first portion extending longitudinally in the bone and the second portion extending longitudinally on the outside of the bone, the arrangement being such that by applying a pulling force to said second portion, a tension force can be developed in said first and second portions, and
a fixation element having means for being secured to said bone and for cooperating with said second portion to maintain said tension force developed in the first and second portions and produce compression of the bone across the fracture site,
said first and second portions being integrally formed and joined together by said bend portion,
said bend portion forming a transition between said first and second portions, said second portion transitioning to a surface adapted to conform with the superficial surface of the bone,
said fixation element comprising a fastener which can pass through a hole in the second portion to secure the second portion directly to the bone at the superficial surface;
wherein the method of forming said implant comprises the steps of:
providing a piece of bar stock of round cross-section having a diameter at least as large as a largest dimension of said legs and said bend,
removing material from the bar stock to form an elongate body comprised of the first and second legs and a region to form the bend, and
bending the elongated body at said region to cause said legs to be juxtaposed and joined by the bend.

32. The method of claim 31, wherein the step of removing material includes forming said second leg first.

* * * * *